US011331109B2

(12) United States Patent
Lee

(10) Patent No.: US 11,331,109 B2
(45) Date of Patent: May 17, 2022

(54) DEVICE AND METHOD FOR AUTOGENOUS BONE GRAFTING

(71) Applicant: EXPLORUS SURGICAL LIMITED, Hong Kong (HK)

(72) Inventor: Kah Hung Benjamino Lee, Hong Kong (HK)

(73) Assignee: EXPLORUS SURGICAL LIMITED, Hong Kong (HK)

( * ) Notice: Subject to any disclaimer, the term of this patent is extended or adjusted under 35 U.S.C. 154(b) by 375 days.

(21) Appl. No.: 16/500,408

(22) PCT Filed: Jul. 31, 2018

(86) PCT No.: PCT/IB2018/055709
§ 371 (c)(1),
(2) Date: Oct. 3, 2019

(87) PCT Pub. No.: WO2019/025957
PCT Pub. Date: Feb. 7, 2019

(65) Prior Publication Data
US 2020/0121328 A1    Apr. 23, 2020

(30) Foreign Application Priority Data

Aug. 4, 2017  (HK) .................. 17107763.1

(51) Int. Cl.
*A61B 17/16*     (2006.01)
*A61B 90/00*     (2016.01)

(52) U.S. Cl.
CPC ...... *A61B 17/1635* (2013.01); *A61B 17/1615* (2013.01); *A61B 17/1637* (2013.01); *A61B 2090/062* (2016.02)

(58) Field of Classification Search
CPC .................. A61B 17/1635; A61B 17/1637
See application file for complete search history.

(56) References Cited

U.S. PATENT DOCUMENTS

| 493,730 A * | 3/1893 | MacKenzie ...... A61B 17/32053 606/179 |
| 6,942,669 B2 * | 9/2005 | Kure .................. A61B 17/1635 606/80 |

(Continued)

*Primary Examiner* — Zade Coley

(57) ABSTRACT

A device (100) and method (1200) for autogenous bone grafting simultaneously cuts a cross-section of a bone (212), both longitudinally with a longitudinal cutting member (104), and transversely with a saw (140) during a bone drilling procedure to obtain a bone block (214) for repairing and rebuilding diseased bones. The device (100) is hand-controllable to selectively cut internally to the device (100), so as to cut captured bone (212) for internal bone harvesting. The device (100) also selectively cuts surrounding bone (212) outside the device (100) for external bone harvesting. The saw (140) is biased to stow in a wall space (120) when not in use, and rotate along a perpendicular plane (202) inwardly or outwardly for internal or external cutting of the bone (212), respectively. The saw (140) rotatably extends inwardly to support and carry the bone block (214) after a longitudinal section has been cut. The saw (140) rotatably extends outwardly from the device (100) to release the bone block (214) after the bone grafting procedure.

20 Claims, 15 Drawing Sheets

(56) References Cited

U.S. PATENT DOCUMENTS

| | | | |
|---|---|---|---|
| 8,920,423 B2 * | 12/2014 | Lee | A61B 17/1635 606/80 |
| 2004/0030343 A1 * | 2/2004 | Kure | A61B 17/1635 606/80 |
| 2004/0034437 A1 * | 2/2004 | Schmieding | A61L 27/52 623/20.14 |
| 2009/0054906 A1 * | 2/2009 | Walthall | A61F 2/4618 606/108 |
| 2011/0232073 A1 * | 9/2011 | Courvoisier | B23B 51/00 29/527.1 |
| 2012/0191096 A1 * | 7/2012 | Lee | A61C 8/0089 606/80 |

* cited by examiner

DEVICE AND METHOD FOR AUTOGENOUS BONE GRAFTING

CROSS REFERENCE OF RELATED APPLICATIONS

This application claims the benefits of Hong Kong short-term patent application no. 17107763.1, filed on Aug. 4, 2017 and entitled BONE HARVESTING DEVICE, which application is incorporated by reference herein in its entirety.

FIELD OF THE INVENTION

The present invention relates generally to a device and method for autogenous bone grafting. More so, the present invention relates to a device that simultaneously cuts a cross-section of a bone, both longitudinally and transversely during a bone drilling procedure to obtain a bone block for repairing and rebuilding diseased bones, and further the device is hand-controllable to selectively cut internally to the device to cut captured bone for internal bone harvesting, and to selectively cut surrounding bone outside the device for external bone harvesting, and whereby the device utilizes the same cutting saw to support and carry the bone block from the drilling insertion point, and then release the bone block which will be used in due course for the grafting operation.

BACKGROUND OF THE INVENTION

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Generally, bone grafting involves grafting a section of bone from one part of the body to another in an effort to strengthen bones that have had operations. For example, bone grafting is very common in orthopedic surgery, neuro/spine surgery, and plastic surgery. Typically, autologous bone grafts are harvested directly from the patient. Autologous bone grafts are inherently biocompatible, osteoconductive, osteoinductive, and osteogenic. Harvesting autologous bone is usually carried out by taking bone from a part of the patient's body other than the surgical site.

Typically, doctors that perform bone graft procedures are commonly orthopedic surgeons, otolaryngology head and neck surgeons, neurosurgeons, craniofacial surgeons, oral and maxillofacial surgeons, periodontists and dentists. Surgeons use bone grafts to repair and rebuild diseased bones in the jaws, spine, hips, knees and other bones and joints. The preferred strategy for most of these operations, including spinal fusions, is the transplantation of structured or morcellized autogenous corticocancellous bone (autograft) from the iliac crest.

Autogenous bone grafting (autograft) has excellent fusion rates and has become the gold standard by which all other biologics are measured against. A bone graft is the basis for every bone fusion. Bone grafting is involved in virtually every major orthopedic and spinal reconstructions. Many surgeons prefer autogenous bone grafts because there is no risk of the body rejecting the graft since it came from the patient's own body.

The current disadvantage of autogenous bone grafting in orthopaedic surgery and spinal surgery is the need for an additional operation which is currently traumatic, resulting in donor site morbidity, blood loss and consumes operation time. The pain and soreness can often last well after the surgery is healed, exceeding the presenting complaint, and there are possible complications such as increased blood loss and prolonged time in the operating room in about 10% to 35% of patients, and varying in severity in these cases, with the use of prior art.

As autogenous bone harvesting is associated with significant morbidities, and the use of alternatives of biological non-autogenous bone blocks have been reported to produce sporadic results of success, there exists a need to provide a device and method for autogenous bone grafting in which the aforesaid shortcomings are mitigated, or at least to provide a useful alternative to the trade and public.

In one prior bone harvesting device as disclosed in GB 2483089A, the initial aim was for the device to be entered into the body and as soon as the depth is reached, the disc is popped-up (dislodged) and thus the spring-loaded saws initially locked within the wall at the bottom end of the device (in the midst of the body) are suddenly unlocked to pounce and press against the bone between them, and as the device continually spins, effectively the bottom of the bone block is cut, via sawing across the base of the captured bone block. The disc merely goes up and down in the vertical plane, a spring biasing it downwards to keep the rod pins in the hole of the saw, thus holding it in place, but once lifted upwards, the saw springs uncontrollably inwards against the bone inside. The disc is merely acting as a lock-down.

In the prior bone harvesting device of GB 2483089A, the rods (attached to the disc above), which pierced through the saws are lifted upwards and no longer hold the spring-loaded saws in place, and the potential energy releases the saws into the bone as a consequence. However, there is no control of the degree of inward cutting, and no limit set for the degree of the saw swinging inwards.

In another prior bone harvesting device as disclosed in GB 2487429A, the disc is spring-loaded with a spring inside the disc which now turns. With first position to keep the saw open, and second position when the saw swings inwards to reach the center of the lumen. Thus, cutting across to the center of the bone block.

So, with the device spinning at high speed, the users (like orthopedic surgeons, otolaryngology head and neck surgeons, neurosurgeons, craniofacial surgeons, oral and maxillofacial surgeons, periodontists and dentists) just dip this device into solid bone to its full depth and the saws will cut the end of the sample, and the user can lift up the device containing the solid bone sample.

However, in these two prior designs, the user must commit the device inside the body to full length before the saw(s) are activated to cut. State differently, there is no control over at any time during the spinning to effect the base cutting as the user's desire.

Other proposals have involved bone grafting devices and methods. The problem with these bone grafting devices is that they do not allow for controllable cutting of the bone, both inwardly for internal bone harvesting, and outwardly for external bone harvesting. Also, the bone grafting devices do not allow the surgeon to control the depth and longitudinal position of the cut. Also, the handle used to control the gripping device is not easily accessible. Even though the above cited gripping devices meets some of the needs of the market, a device and method for autogenous bone grafting. More so, the present invention relates to a device that simultaneously cuts a cross-section of a bone, both longitudinally and transversely during a bone drilling procedure to obtain a bone block for repairing and rebuilding diseased bones, and further the device is hand-controllable to selectively cut internally to the device to cut captured bone for internal bone harvesting, and to selectively cut surrounding bone outside the device for external bone harvesting, and whereby the device utilizes the same cutting saw to support and carry the bone block from the drilling insertion point, and then release the bone block after the grafting operation, is still desired.

SUMMARY

Illustrative embodiments of the disclosure are generally directed to a device and method for autogenous bone grafting. The device and method serves to cut a cross-section of a bone during a bone drilling procedure to obtain a bone block for repairing and rebuilding diseased bones, and which is suitable for medical surgery including orthopedic surgery, spinal surgery, oral surgery and plastic surgery.

In one embodiment, the device and method for autogenous bone grafting simultaneously cuts a cross-section of a bone, both longitudinally with a longitudinal cutting member, and transversely with a saw during a bone drilling procedure to obtain a bone block for repairing and rebuilding diseased bones. The device is hand-controllable to selectively cut internally to the device, so as to cut captured bone for internal bone harvesting. The device also selectively cuts surrounding bone outside the device for external bone harvesting. The saw is biased to stow in a wall space when not in use, and rotate along a perpendicular plane inwardly or outwardly for internal or external cutting of the bone, respectively. The saw rotatably extends inwardly to support and carry the bone block after a longitudinal section has been cut. The saw rotatably extends outwardly from the device to release the bone block after the bone grafting procedure.

In some embodiments, the device may include a longitudinal cutting member being defined by an upper end and a lower end forming an opening to a cavity. The longitudinal cutting member is further defined by a wall forming a wall space. The lower end of the longitudinal cutting member comprises a plurality of cutting teeth. The longitudinal cutting member is rotatable about a longitudinal axis.

In some embodiments, the device may include a drill shaft that is joined with the upper end of the longitudinal cutting member. The drill shaft is substantially aligned with the longitudinal axis of the longitudinal cutting member. In yet other embodiments, a motorized drill joins with the drill shaft. The motorized drill rotatably drives the drill shaft and the longitudinal cutting member. Due to this orientation, the cutting teeth of the longitudinal cutting member are operable to enable longitudinal cutting through a bone.

In some embodiments, the device may include a rod that is defined by a top end and a bottom end. The rod is rotatable about a pivoting axis. The pivoting axis is disposed in a spaced-apart, parallel relationship with the longitudinal axis.

In some embodiments, the device may include at least one saw joined with the bottom end of the rod, and proximal to the lower end of the longitudinal cutting member. The saw is rotatable along a plane perpendicular to the pivoting axis. Due to this orientation, the saw is operable to enable transversal cutting through the bone.

The saw rotatably articulates along the plane between a first position substantially inside the wall space of the wall, and a second position extended between the wall and the longitudinal axis of the longitudinal cutting member. The saw rotatably articulates along the plane between the first position and a third position partially extended between the wall space and an external area outside the cavity of the longitudinal cutting member.

In some embodiments, the device may include a saw gear that is defined by a plurality of saw teeth. The saw gear joins with the top end of the rod. Additionally, the device comprises a disc that is in engagement with the drill shaft. The disc is configured to advance along the drill shaft towards the motorized drill. The disc is also configured to advance along the drill shaft away from the motorized drill. The disc comprises disc teeth disposed in meshed engagement with the saw teeth.

In some embodiments, the device may include a spring disposed around the drill shaft. The spring biases the disc away from the motorized drill to the first position. Additionally, a helical member is disposed in the hole of the disc. The helical member is in engagement with the disc and the drill shaft. In this manner, the helical member causes the disc to rotate clockwise while advancing towards the motorized drill; whereby the helical member causes the disc to rotate counterclockwise while advancing away from the motorized drill.

Further, when the disc advances along the drill shaft towards the motorized drill, the disc teeth rotate against the saw teeth, causing the saw gear to rotate in an anticlockwise direction, causing the rod and the saw to rotate in the anticlockwise direction to the second position. Thus, when the disc advances along the drill shaft away from the motorized drill, the disc teeth rotate against the saw teeth, causing the saw gear to rotate in a clockwise direction, causing the rod and the saw to rotate in the clockwise direction to the third position.

In some embodiments, the device may include a disc cap that is joined with the disc and concentrically encircling the drill shaft. Further, the device comprises an interconnecting lever defined by an actuation end and a cap end joined with the disc cap. The interconnecting lever pivotally articulates about a hinge on the motorized drill. In this manner, depressing the actuation end of the interconnecting lever displaces the disc towards the motorized drill, causing the saw to rotate in the anticlockwise direction to the second position. Further, lifting the actuation end of the interconnecting lever displaces the disc away from the motorized drill, causing the saw to rotate in the clockwise direction to the third position.

So, the device is such that it spins to enter into the body, and then armed with a convenient control interconnecting lever to function the saws at the tip of the hollow longitudinal cutting member, it can be lifted up or down in order to (via the interconnecting lever attached loosely around the recess space above the disc) to in effect alter the vertical position of the disc which in turn, via the internal wheel and rod and is connected to the saw at the apical end of the device to effectively cut across a plane substantially perpendicular to the pivoting axis, and to any degree or full extents as the operator sees fit and wishes upon.

The operator can choose to drill down into the body to any length desired, and from there, either to cut across into the bone, to full extents whereby the tip of the saw reaches the center of the lumen to completely section a solid bone sample, and withdraw the device to collect a clean-cut bone sample, in exact measures; or in the case of the femor, to section outside of the device, and separate the upper portion of the femur head; retract the saws back to default position and remove the device.

In another aspect, the longitudinal cutting member comprise a cylindrical shape.

In another aspect, the longitudinal cutting member comprises a cutting member shoulder.

In another aspect, the longitudinal cutting member forms a drill tunnel extending through the wall.

In another aspect, the rod passes through the drill tunnel.

In another aspect, the lower end of the longitudinal cutting member comprises an open vertical window for accommodating the rod.

In another aspect, the disc forms a hole sized and dimensioned to receive the drill shaft.

In another aspect, the saw comprises a tip end and a base end joined with the bottom end of the rod.

In another aspect, the helical member comprises a calibrated threaded screw.

In another aspect, the hinge is disposed on the motorized drill.

In another aspect, the actuation end of the interconnecting lever comprises a handle.

In another aspect, the interconnecting lever is pivotable relative to the recess of the disc cap.

In another aspect, the device further comprises a U-shaped connecting member joined with the cap end of the interconnecting lever.

In another aspect, the disc cap is defined by a recess that receives the U-shaped connecting member.

In another aspect, the device further comprises a gauge scale between the actuation end of the interconnecting lever and the motorized drill.

In another aspect, the device further comprises a vertical gauge disposed along the length of the longitudinal cutting member.

One objective of the present invention is to provide a transversally cutting saw that rotates along a perpendicular plane inwardly or outwardly for internal or external cutting of the bone, respectively.

Another objective is to enable the operating surgeon to cut a cylindrical block of bone of a certain length, and that is evenly divided into two or three sections, and that is utilized as two or three discs.

Another objective is to rotatably extend the saw inwardly to support and carry the bone block after a longitudinal section has been cut.

Another objective is to rotatably extend the saw outwardly from the device to release the bone block after the bone grafting procedure.

Another objective is provide control of the saw with an interconnecting lever that is easily controlled by the thumb.

Yet another objective is to provide a bone grafting device that is suitable for medical surgery including orthopedic surgery, spinal surgery, oral surgery and plastic surgery.

Other systems, devices, methods, features, and advantages will be or become apparent to one with skill in the art upon examination of the following drawings and detailed description. It is intended that all such additional systems, methods, features, and advantages be included within this description, be within the scope of the present disclosure, and be protected by the accompanying claims and drawings.

BRIEF DESCRIPTION OF THE DRAWINGS

The invention will now be described, by way of example, with reference to the accompanying drawings, in which:

FIG. 5A illustrates a cylindrical block of bone partially divided into two segments, and FIG. 5B illustrates a cylindrical block of bone completely divided into two segments, in accordance with an embodiment of the present invention;

Like reference numerals refer to like parts throughout the various views of the drawings.

DETAILED DESCRIPTION OF THE INVENTION

The following detailed description is merely exemplary in nature and is not intended to limit the described embodiments or the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to make or use the embodiments of the disclosure and are not intended to limit the scope of the disclosure, which is defined by the claims. For purposes of description herein, the terms "upper," "lower," "left," "rear," "right," "front," "vertical," "horizontal," and derivatives thereof shall relate to the invention as oriented in FIG. 1. Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Specific dimensions and other physical characteristics relating to the embodiments disclosed herein are therefore not to be considered as limiting, unless the claims expressly state otherwise.

A device 100 and method 1200 for autogenous bone grafting is referenced in FIGS. 1-12. The device 100 is configured to cut a cross-section of a bone 212 during a bone drilling procedure to obtain a bone block 214 for repairing and rebuilding diseased bones, and which is suitable for medical surgery including orthopedic surgery, spinal surgery, oral surgery and plastic surgery.

Figure 1:
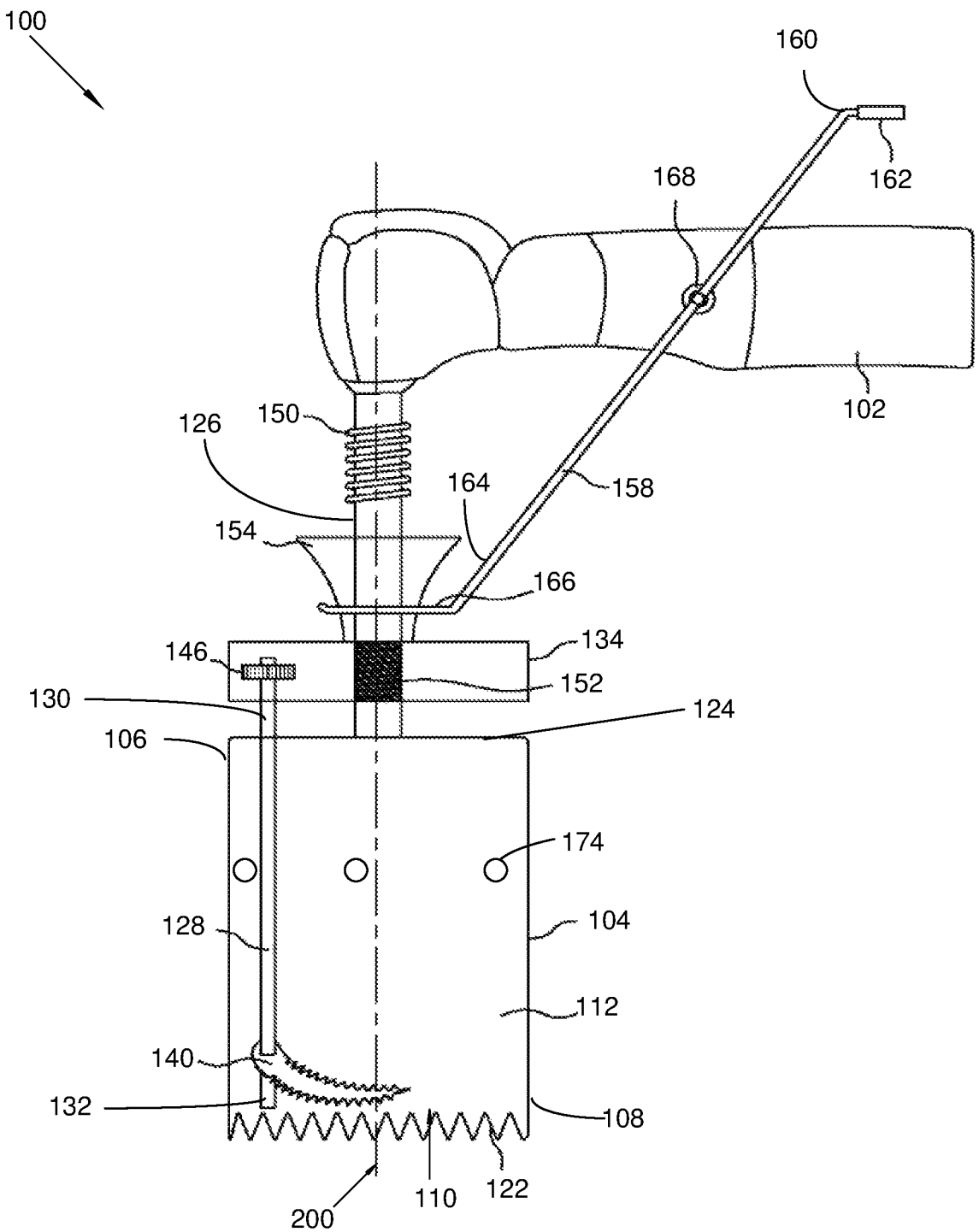
FIG. 1 illustrates a perspective view of an exemplary device for autogenous bone grafting, showing a longitudinal cutting member being rotatably driven by a motorized drill, in accordance with an embodiment of the present invention.
Figure 2:
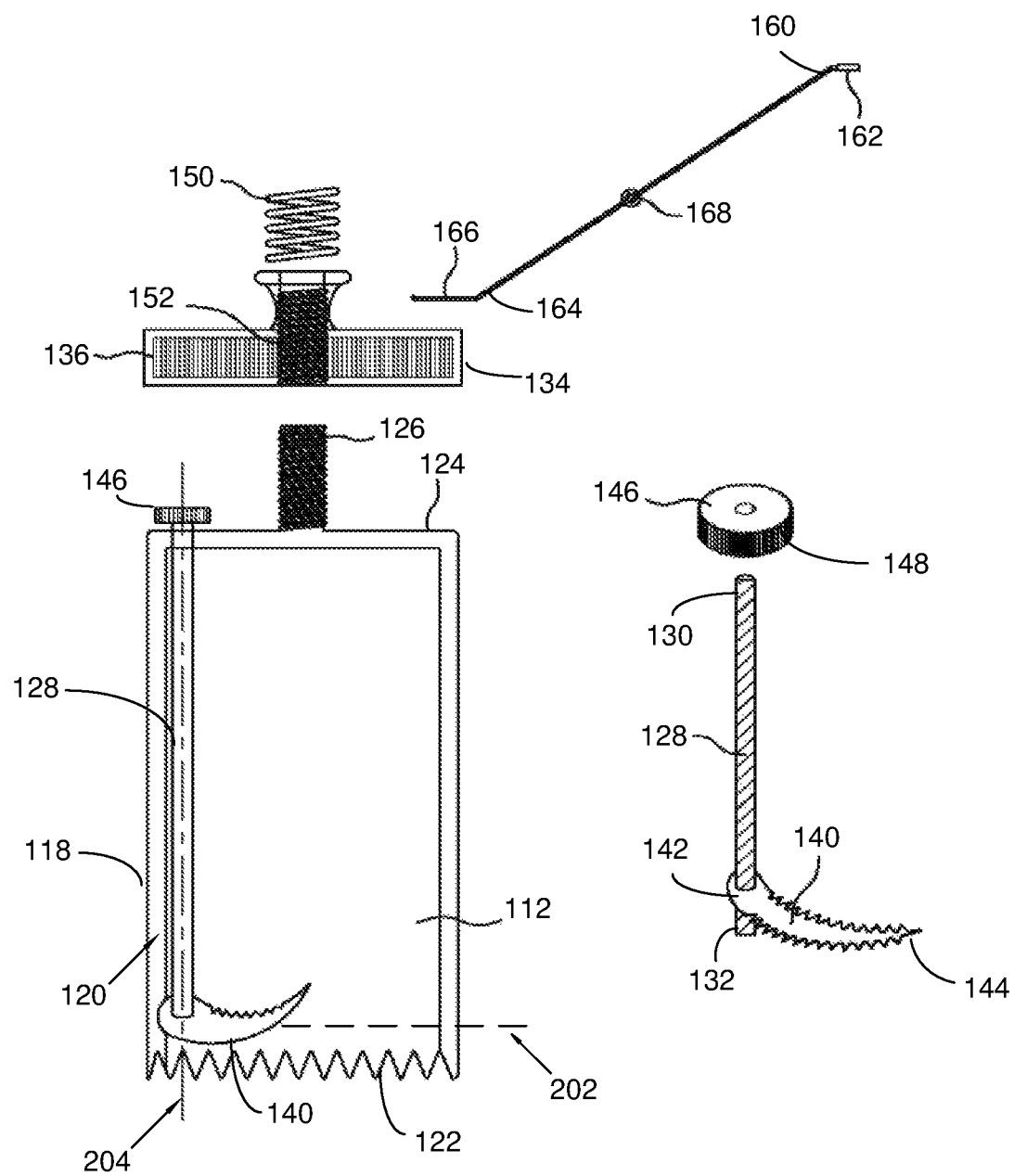
FIG. 2 illustrates a sectional view of an exemplary longitudinal cutting member and an exploded view of an exemplary rod with an attached saw, in accordance with an embodiment of the present invention.

As referenced in FIG. 1, a device 100 for autogenous bone grafting, hereafter "device 100" according to an embodiment of the present invention is shown in FIGS. 1 and 2, and generally designated as 100. The various components forming the device 100 are all separable from one another and thus individually replaceable.

The device 100 is configured to selectively cut a cross-section of a bone 212 during a bone drilling procedure to obtain a bone block 214 for repairing and rebuilding diseased bones. In one embodiment, the device 100 and method 1200 for autogenous bone grafting simultaneously cuts a cross-section of a bone 212, both longitudinally with a longitudinal cutting member 104, and transversely with a saw 140 during a bone drilling procedure to obtain a bone block 214 for repairing and rebuilding diseased bones.

The device 100 is hand-controllable to selectively cut internally to the device 100, so as to cut captured bone 212 for internal bone harvesting. The device 100 also selectively cuts surrounding bone 212 outside the device 100 for external bone harvesting. The saw 140 is biased to stow in a wall space 120 when not in use, and rotate along a perpendicular plane 202 inwardly or outwardly for internal or external cutting of the bone 212, respectively. The saw 140 rotatably extends inwardly to support and carry the bone block 214 after a longitudinal section has been cut. The saw 140 rotatably extends outwardly from the device 100 to release the bone block 214 after the bone grafting procedure.

Figure 2A:
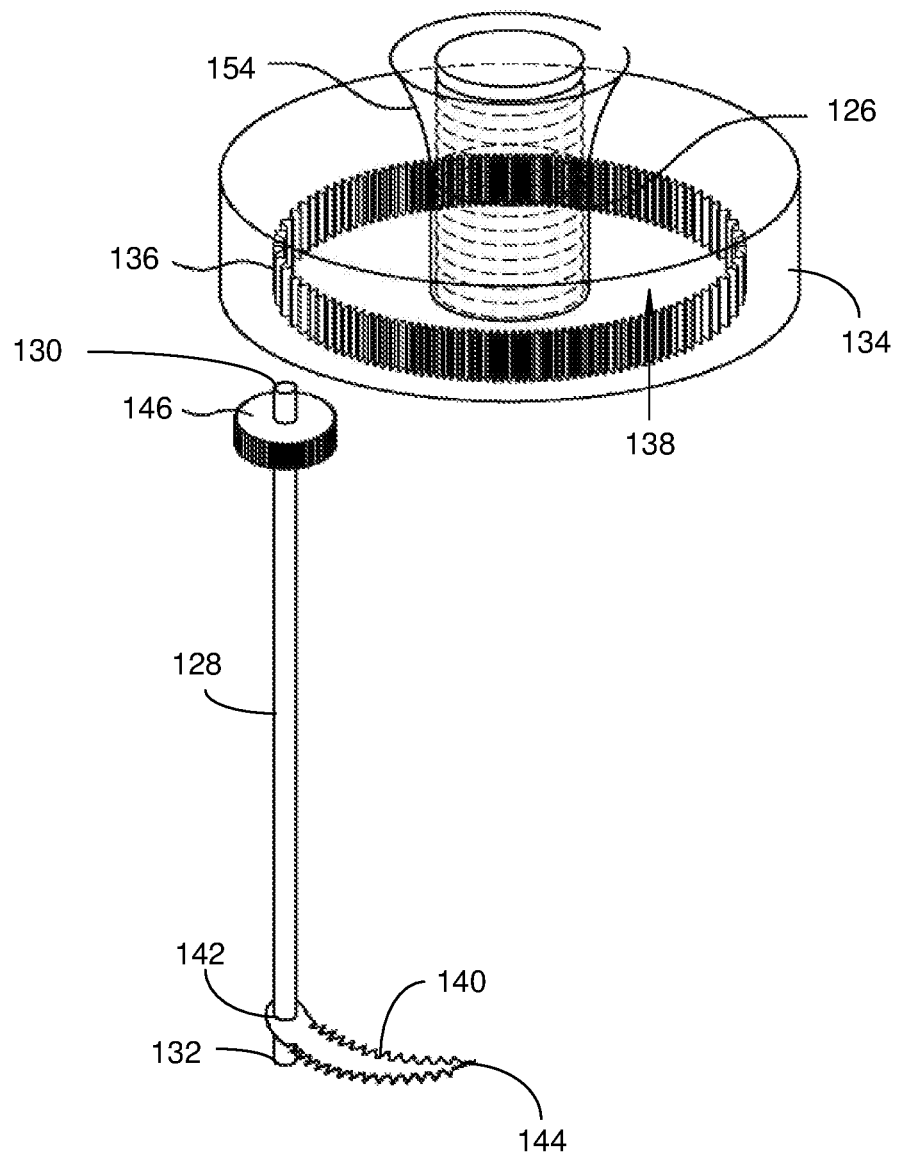
FIG. 2A illustrates a perspective view of an exemplary rod with an attached saw, and a disc with disc teeth that mesh with the saw teeth, in accordance with an embodiment of the present invention.
Figure 2B:
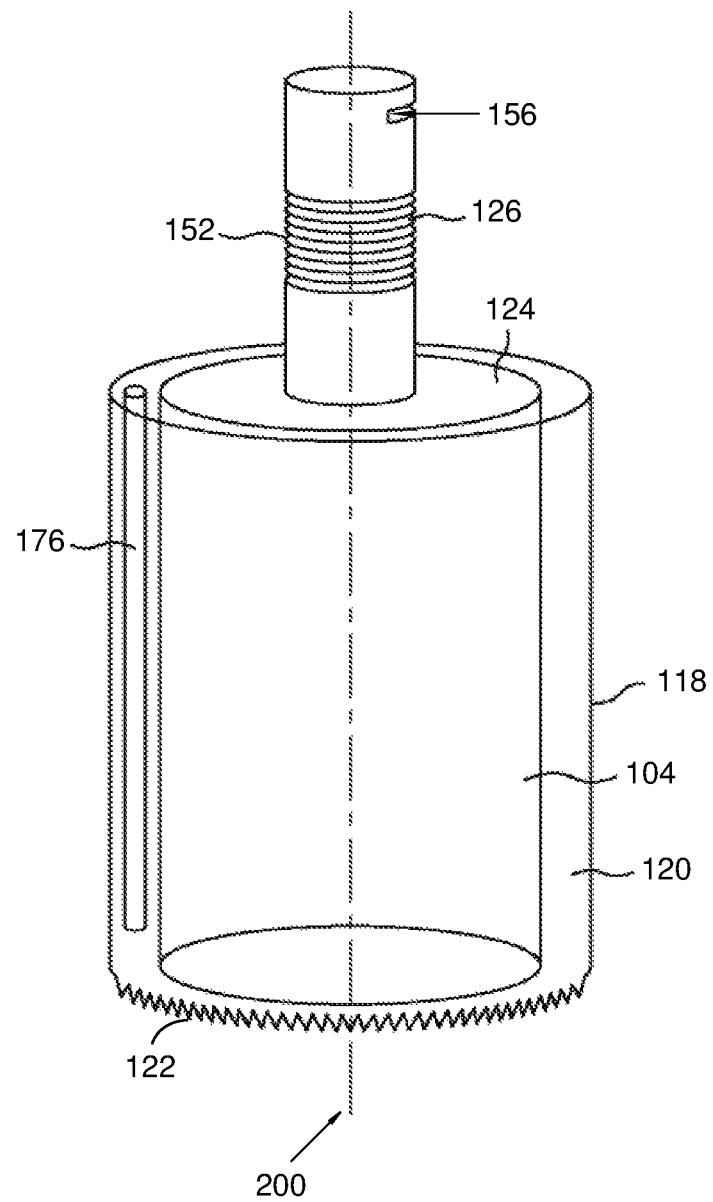
FIG. 2B illustrates a perspective view of an exemplary longitudinal cutting member, in accordance with an embodiment of the present invention.

As illustrated in FIG. 2B, the device 100 may include a longitudinal cutting member 104 that is defined by an upper end 106 and a lower end 108. The lower end 108 forms an opening 110 to a cavity 112. The longitudinal cutting member 104 is further defined by a wall 118 forming a wall space 120. The lower end 108 of the longitudinal cutting member 104 comprises a plurality of cutting teeth 122. The longitudinal cutting member 104 is rotatable about a longitudinal axis 200. In one non-limiting embodiment, the longitudinal cutting member 104 comprise a cylindrical shape.

In some embodiments, the longitudinal cutting member 104 may include a cutting member shoulder 124. In some embodiments, the longitudinal cutting member 104 forms a drill tunnel 176 extending through the wall 118. In one alternative embodiment, the lower end 108 of the longitudinal cutting member 104 comprises an open vertical window 116 for accommodating the rod 128. In one non-limiting embodiment, the device 100 further comprises a vertical gauge 172 disposed along the length of the longitudinal cutting member 104.

Looking again at FIG. 2, the device 100 may include a drill shaft 126 that is joined with the upper end 106 of the longitudinal cutting member 104. The drill shaft 126 is substantially aligned with the longitudinal axis 200 of the longitudinal cutting member 104. In yet other embodiments, a motorized drill 102 joins with the drill shaft 126. The motorized drill 102 rotatably drives the drill shaft 126 and the longitudinal cutting member 104. Due to this orientation, the cutting teeth 122 of the longitudinal cutting member 104 are operable to enable longitudinal cutting through a bone 212.

Figure 2C:
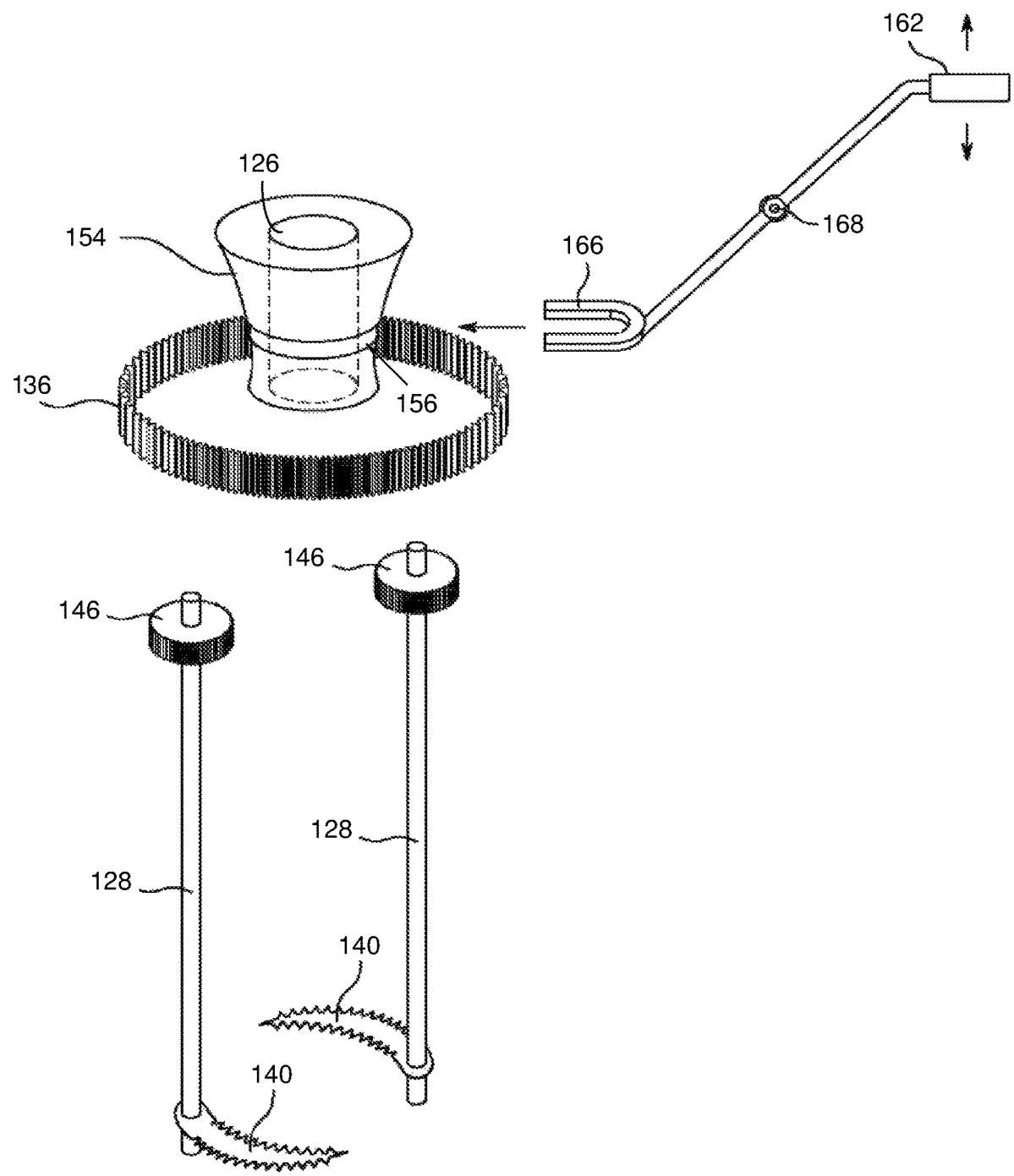
FIG. 2C illustrates a perspective view of an exemplary interconnecting lever and rods with attached saws, in accordance with an embodiment of the present invention.

As shown in FIG. 2C, the device 100 may include a rod 128 that is defined by a top end 130 and a bottom end 132. The rod 128 may pass through the drill tunnel 176. The rod 128 is rotatable about a rod axis 204. The rod axis 204 is disposed in a spaced-apart, parallel relationship with the longitudinal axis 200.

In some embodiments, the device 100 may include at least one saw 140 joined with the bottom end 132 of the rod 128, and proximal to the lower end 108 of the longitudinal cutting member 104. The saw 140 is rotatable along a plane 202 perpendicular to the rod axis 204. Due to this orientation, the saw 140 is operable to enable transversal cutting through the bone 212. The saw 140 may include a tip end 144 and a base end 142 joined with the bottom end 132 of the rod 128. In some embodiments, the saw 140 may include a bone microsaw or a cutter.

Figure 3A:
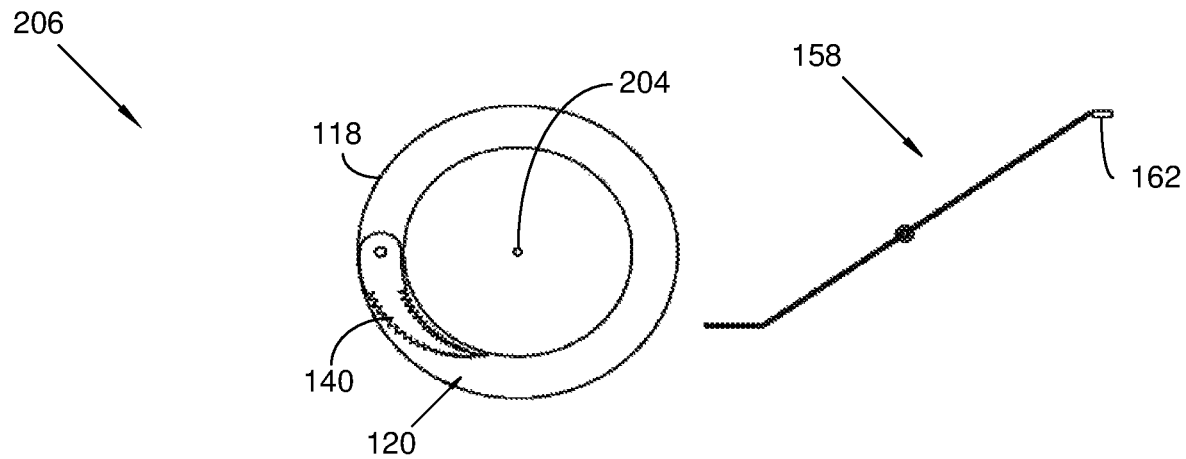
FIGS. 3A, 3B, and 3C illustrate top view of the saw moving from the first position to the second position, in accordance with an embodiment of the present invention.
Figure 3B:
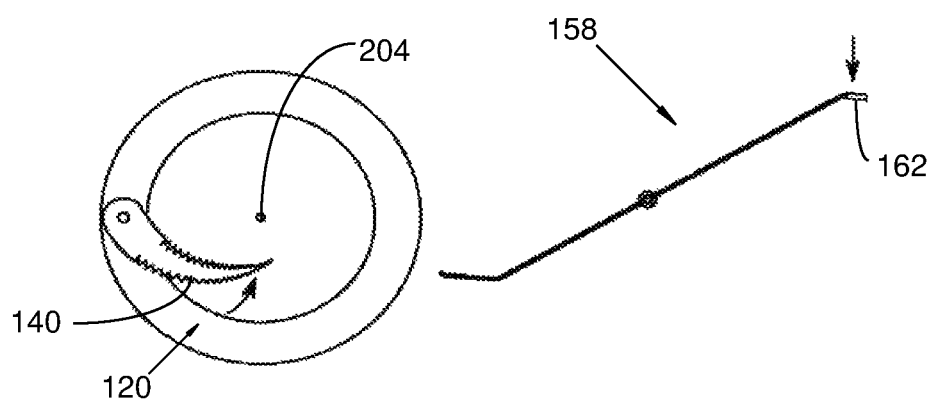
Figure 3C:
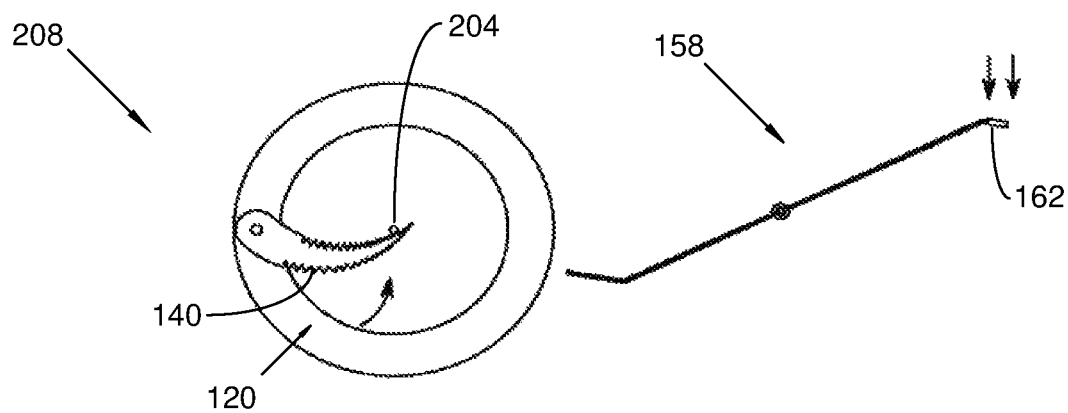
Figure 4:
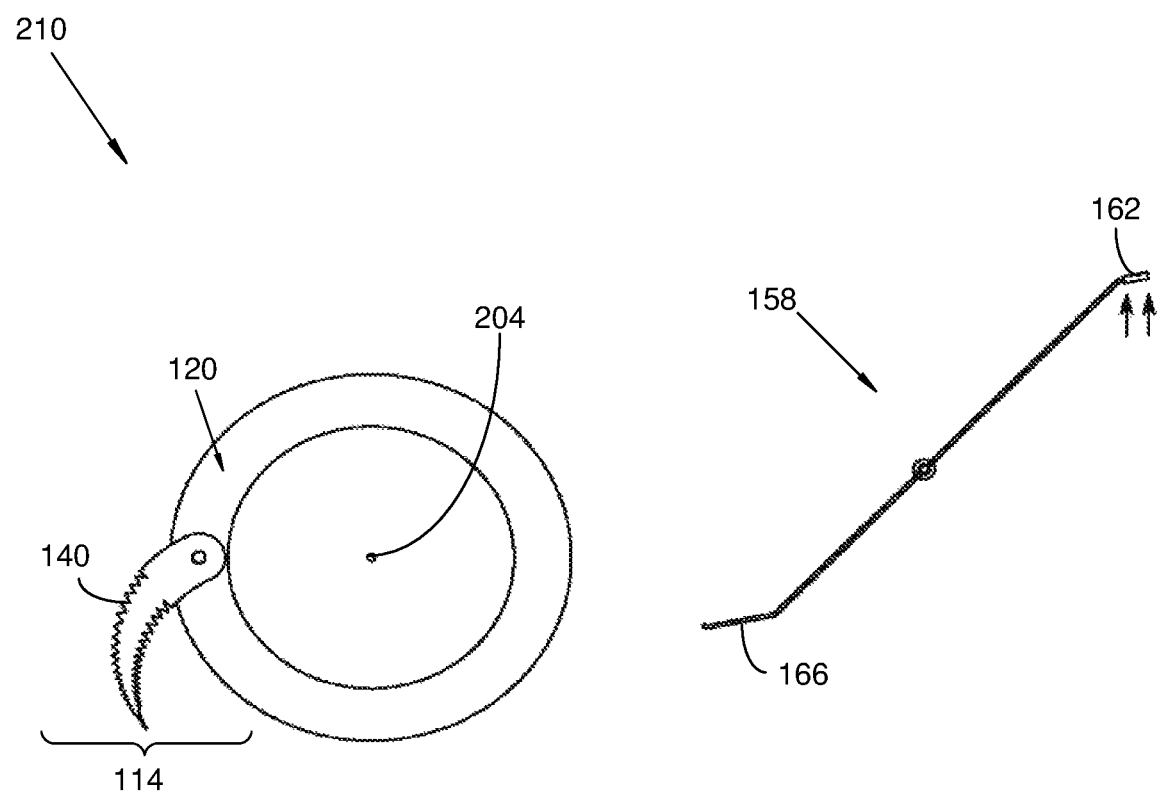
FIG. 4 is a schematic bottom view of the device of FIG. 1 with the saw extended to a third position, in accordance with an embodiment of the present invention.

As shown in FIGS. 3A, 3B, and 3C, the saw 140 rotatably articulates along the plane 202 between a first position 206 substantially inside the wall space 120 of the wall 118, and a second position 208 extended between the wall 118 and the longitudinal axis 200 of the longitudinal cutting member 104. As further shown in FIG. 4, the saw 140 rotatably articulates along the plane 202 between the first position 206 and a third position 210 partially extended between the wall space 120 and an external area 114 outside the cavity 112 of the longitudinal cutting member 104.

Looking again at FIG. 2C, the device 100 include a saw gear 146 that is defined by a plurality of saw teeth 148. The saw gear 146 joins with the top end 130 of the rod 128. Additionally, the device 100 comprises a disc 134 that is in engagement with the drill shaft 126. The disc 134 is configured to advance along the drill shaft 126 towards the motorized drill 102. The disc 134 is also configured to advance along the drill shaft 126 away from the motorized drill 102. The disc 134 comprises disc teeth 136 disposed in meshed engagement with the saw teeth 148. The disc 134 forms a hole 138 that is sized and dimensioned to receive the drill shaft 126.

In some embodiments, the device 100 may include a spring 150 disposed around the drill shaft 126. The spring 150 biases the disc 134 away from the motorized drill 102 to the first position 206. Additionally, a helical member 152 is disposed in the hole 138 that concentrically forms in the disc 134. The helical member 152 is in engagement with the disc 134 and the drill shaft 126. In this manner, the helical member 152 causes the disc 134 to rotate clockwise while advancing towards the motorized drill 102. Thus, the helical member 152 causes the disc 134 to rotate counterclockwise while advancing away from the motorized drill 102. In one non-limiting embodiment, the helical member 152 comprises a calibrated threaded screw.

Further, when the disc 134 advances along the drill shaft 126 towards the motorized drill 102, the disc teeth 136 rotate against the saw teeth 148, causing the saw gear 146 to rotate in an anticlockwise direction. This in turn causes the rod 128 and the saw 140 to rotate in the anticlockwise direction to the second position 208. Thus, when the disc 134 advances along the drill shaft 126 away from the motorized drill 102, the disc teeth 136 rotate against the saw teeth 148, which causes the saw gear 146 to rotate in a clockwise direction, which enables the rod 128 and the saw 140 to rotate in the clockwise direction to the third position 210.

In some embodiments, the device 100 may include a disc cap 154 that is joined with the disc 134. The disc cap 154 also concentrically encircles the drill shaft 126. Further, the device 100 comprises an interconnecting lever 158 defined by an actuation end 160 and a cap end 164 joined with the disc cap 154. The interconnecting lever 158 pivotally articulates about a hinge 168 on the motorized drill 102. In one non-limiting embodiment, the hinge 168 is disposed centrally on the motorized drill 102 (FIG. 1). In some embodiments, the device 100 may further include a U-shaped connecting member 166 that is joined with the disc cap 154 of the interconnecting lever 158. The disc cap 154 is defined by a recess 156 that receives the U-shaped connecting member 166.

The interconnecting lever 158 is pivotable relative to the recess 156 of the disc cap 154. The actuation end 160 of the interconnecting lever 158 comprises a handle 162 that can be depressed or lifted to effect the position of the saw 140. In this manner, depressing the actuation end 160 of the interconnecting lever 158 displaces the disc 134 towards the motorized drill 102, causing the saw 140 to rotate in the anticlockwise direction to the second position 208. Further, lifting the actuation end 160 of the interconnecting lever 158 displaces the disc 134 away from the motorized drill 102, causing the saw 140 to rotate in the clockwise direction to the third position 210.

Figure 11:
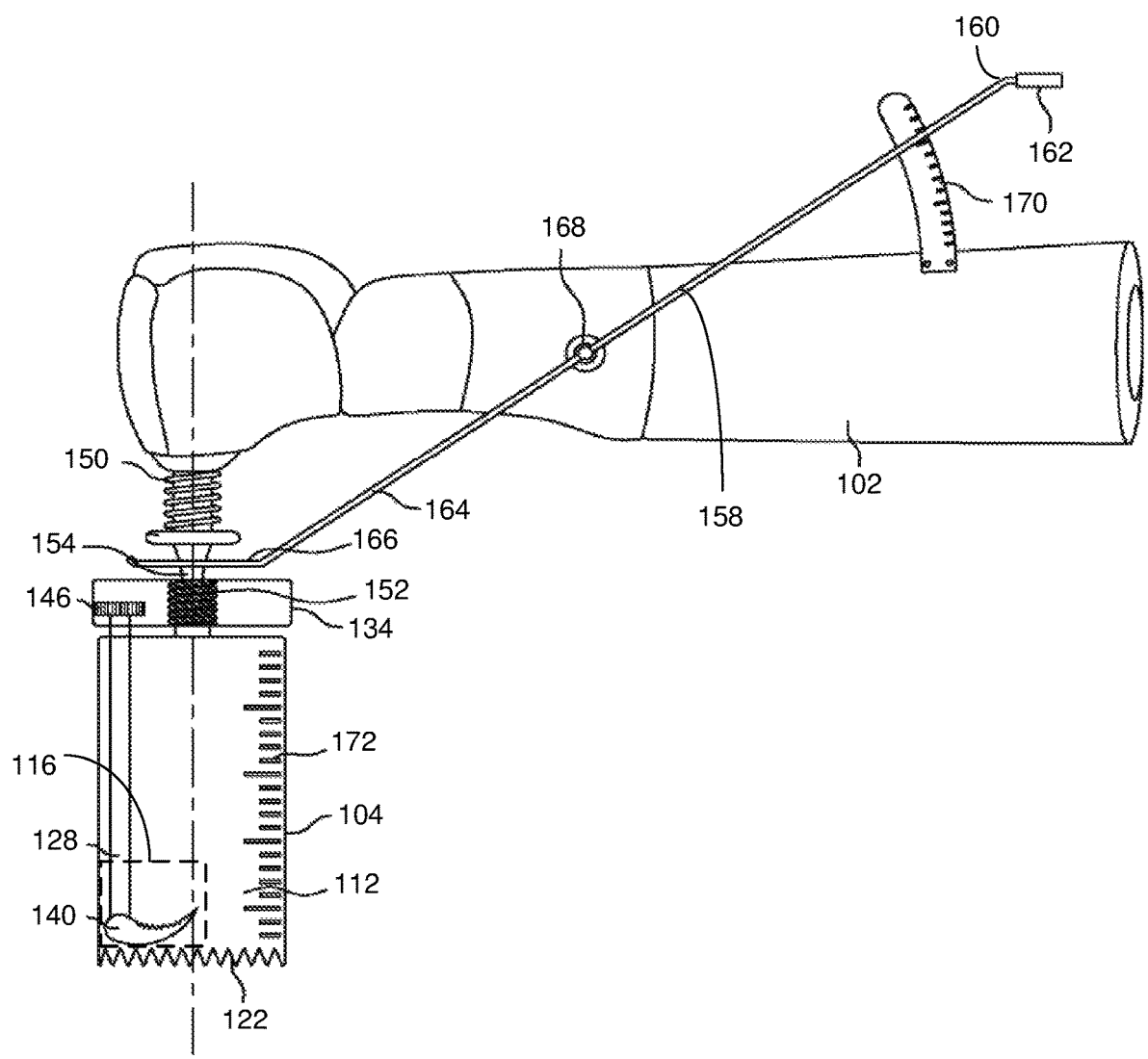
FIG. 11 illustrates a gauge scale between the interconnecting lever and the drill, and a vertical gauge running the length of the longitudinal cutting member, in accordance with an embodiment of the present invention.

As illustrated in FIG. 11, the device 100 further comprises a gauge scale 170 that is disposed between the actuation end 160 of the interconnecting lever 158 and the motorized drill 102. The gauge scale 170 helps the surgeon cut transversely across the bone 212 in a precise manner. The gauge scale 170 may have millimeter markings alongside the handle 162 of the device 100 can be included to serve to precisely indicate the depth of saw cutting into the bone 212 during the active process in real time.

Further, the device 100 also includes a vertical gauge 172 with millimeter markings on the outside and alongside the longitudinal cutting member 104 which serves to indicate the depth entered by the longitudinal cutting member 104 into the body (pelvis, sacrum, ribs, or other suitable bones of the human body). In this way, the device 100 offers unprecedented precision for the extraction of bone 212, whether for therapeutic purposes (bone grafting) or for bone sample analysis, or also for harvesting bone marrow for analysis in metabolic and renal medical diseases.

With reference to FIG. 11, with the precision requirements for bone grafting, the gauge scale 170 and the vertical gauge 172 provide factory-set millimeter markings. These markings enable the surgeon to drill down into the body to a depth of about 2 mm, and then depress the interconnecting lever 158, to create an across-cut groove into the bone block 214 inside the drill just 1 mm indentation groove, lift the lever 158 to default, and then drill down another 2 mm to make another across-cut groove of 1 mm indentation. Such grooves can be cut in such a manner all the way down the full length of the longitudinal cutting member 104.

At the final groove, the lever 158 can be fully depressed when the saw 140 cuts across the center point (central axis of the lumen) and completely section the bone block 214, and keeping the lever 158 depressed at that point, withdraw the entire device 100 out of the body with a full bone block 214 inside, with a series of 1 mm indented grooves along its length at 2 mm intervals. This is a demonstration of the control this instrument device offers, and this high level of precision and control is unprecedented.

Thus, the longitudinal cutting member 104 spins to enter into the body, and then armed with an interconnecting lever 158 to function the saw 140 at the tip of the hollow longitudinal cutting member 104, it can be lifted up or down in order to (via the interconnecting lever 158 attached loosely around the recess 156 above the disc 134) to in effect alter the vertical position of the disc 134 which in turn, via the internal wheel and rod 128 and is connected to the saw 140 at the apical end of the device 100 to effectively cut across the plane 202 that is perpendicular to the rod axis 204.

Figure 8:
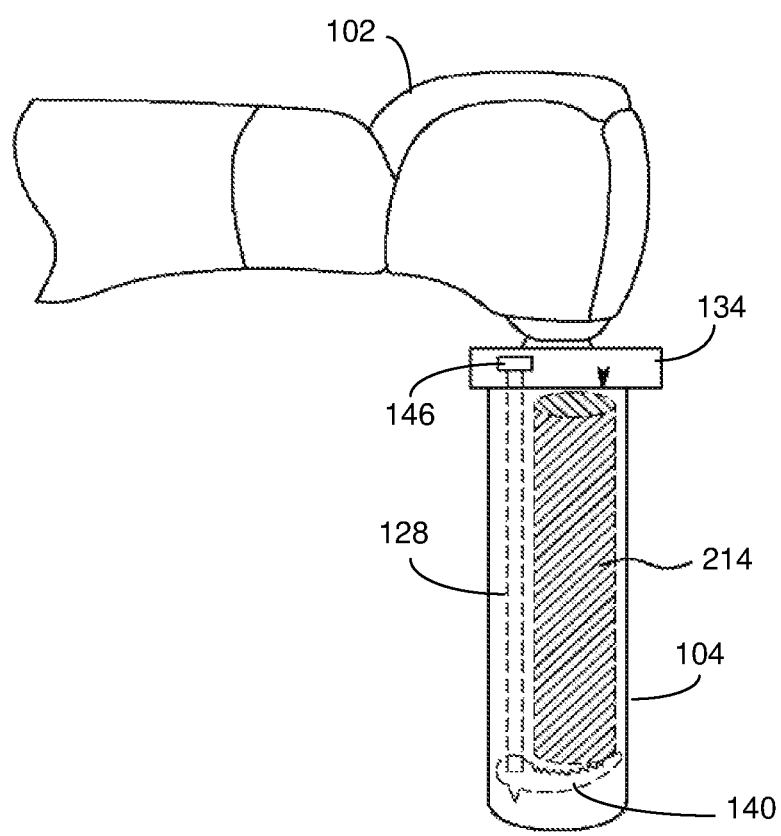
FIG. 8 illustrates the harvesting of bone when a second position of the saw is effected by the device shown in FIG. 1, in accordance with an embodiment of the present invention.
Figure 9:
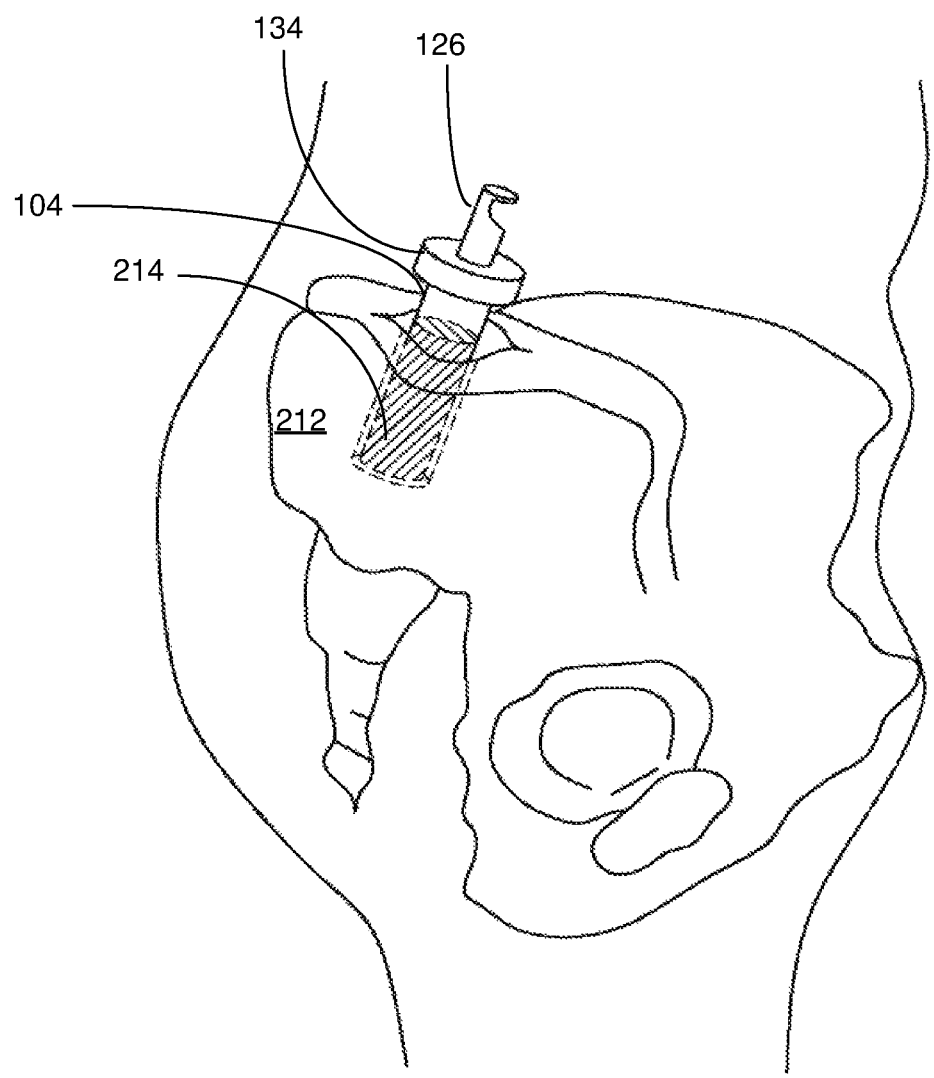
FIG. 9 illustrates a way of using a bone harvested by the device shown in FIG. 1, in accordance with an embodiment of the present invention.

The operator can choose to drill down into the body to any length desired, and from there, either to cut across into the bone 212, to full extents whereby the tip of the saw 140 reaches the center of the lumen to completely section a solid bone sample, and withdraw the device 100 to collect a clean-cut sample of a bone block 214, in exact measures (FIG. 8). Or in the case of the femur, to section outside of the longitudinal cutting member 104, and separate the upper portion of the femur head; retract the saw 140 back to default position and remove the longitudinal cutting member 104 from the insertion point.

The advantages of this feature is that sometimes the operating surgeon desires a cylindrical block of bone 212 of a certain length, which is evenly divided into two or three sections, and utilized as two or three discs. For example, for the bone disc to be used to replace the degenerated spinal discs which require to be removed, and replaced by bone in spinal fusion procedures. This depends on how many spinal discs are diseased, whether it is one, two, three, or maybe more. Also, whilst the diameter of the bone graft required can be uniform, including 16 mm diameter suffices. However ion other embodiments, the length may vary from 5 mm to 7 mm, to 9 mm.

Figure 5A:
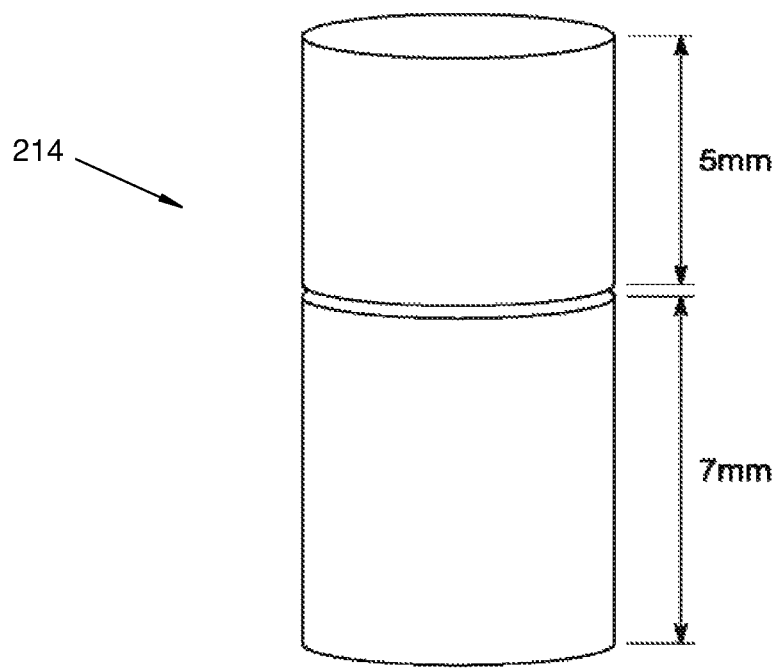
FIGS. 5A and 5B illustrate the cylindrical block of bone which can be harvested by the device of FIG. 1, where
Figure 5B:
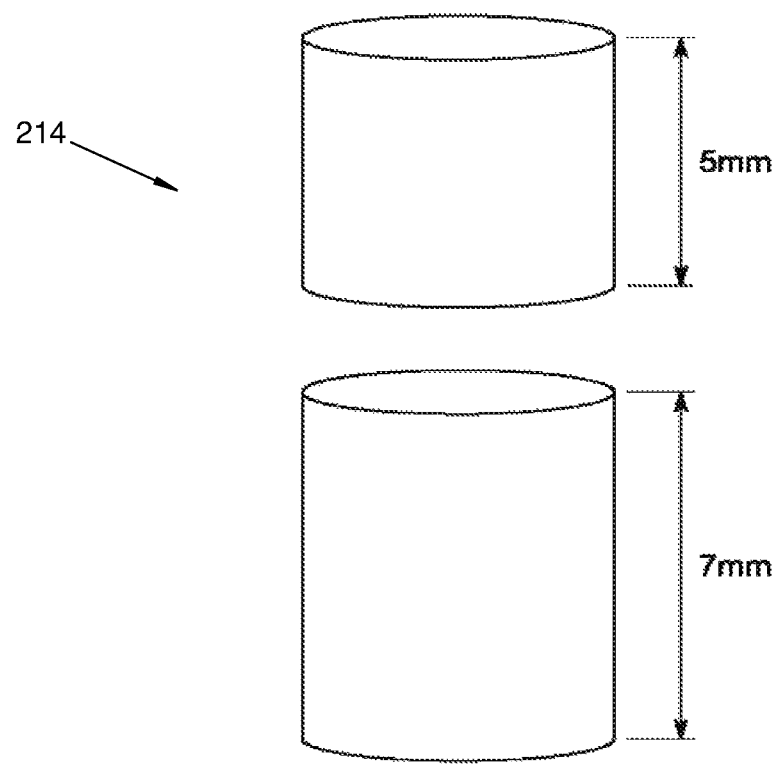
Figure 10:
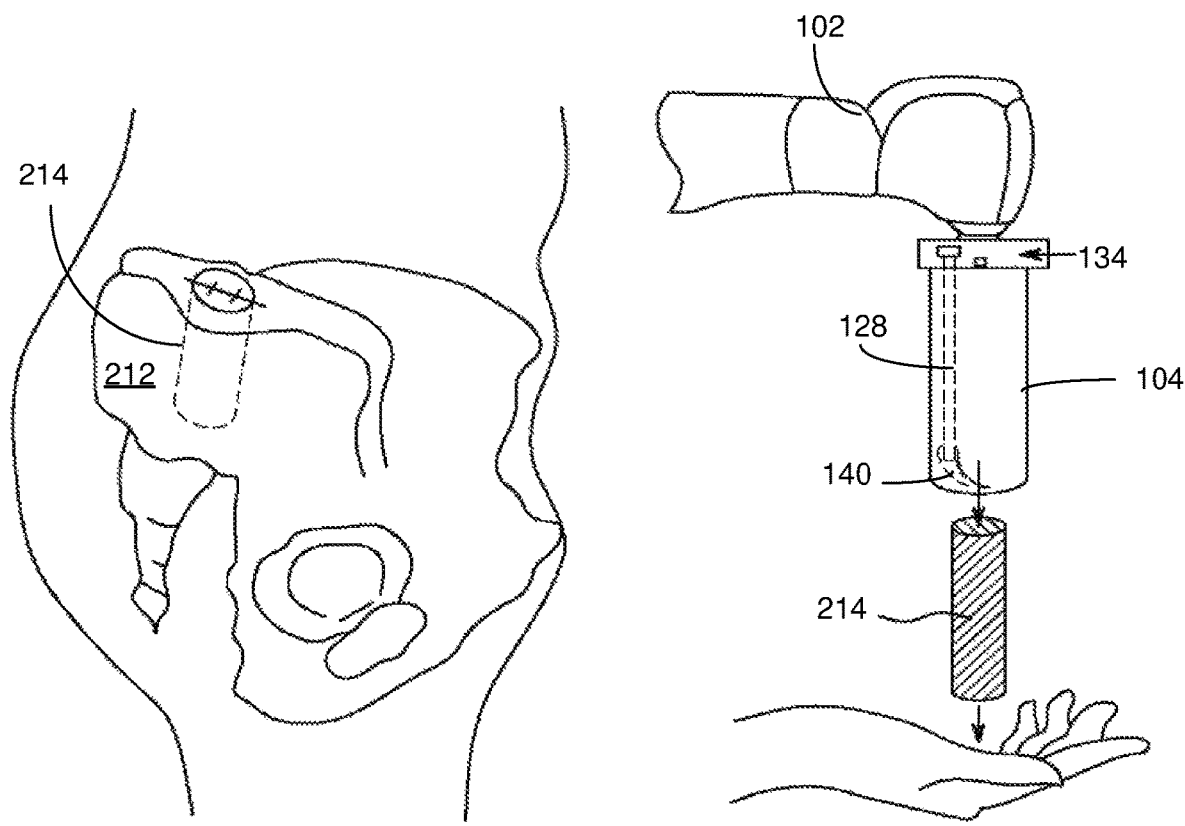
FIG. 10 demonstrates the delivery of an autogenous bone block (autograft) harvested with the device shown in FIG. 1, and also illustrates a block of bone harvested from the iliac crest bone, in accordance with an embodiment of the present invention.

As shown in FIG. 10, if two discs are desired, one at a length of 5 mm, and another at a length of 7 mm; the surgeon utilizes the longitudinal cutting member 104 to drill into the pelvis to a depth of 5 mm, depress the interconnecting lever 158 slightly to make a marking, retract the interconnecting lever 158 and continue the drilling downwards about 12 mm, and fully depress the interconnecting lever 158 for a complete sectioning and subsequently withdraw to extract the entire cylindrical block. With the bone graft block in hand, the surgeon can see the 5 mm marking and may decide or may not decide to proceed with actually sectioning the bone 212 into two discs with using a common orthopedic saw, depending on the real time clinical situation of the spine disorder (FIGS. 5A, 5B, and 10).

The operator may choose to utilize the entire block piece meal if also the vertebrae bodies exhibit extensive degeneration and must be partially removed in addition to the diseased intervertebral discs. In the case of the lumbar spine, the treatment thus can be upgraded from a simple discs replacements to a lumbar cortectomy, in which case some portions of the vertebrae are also involved.

Figure 12:
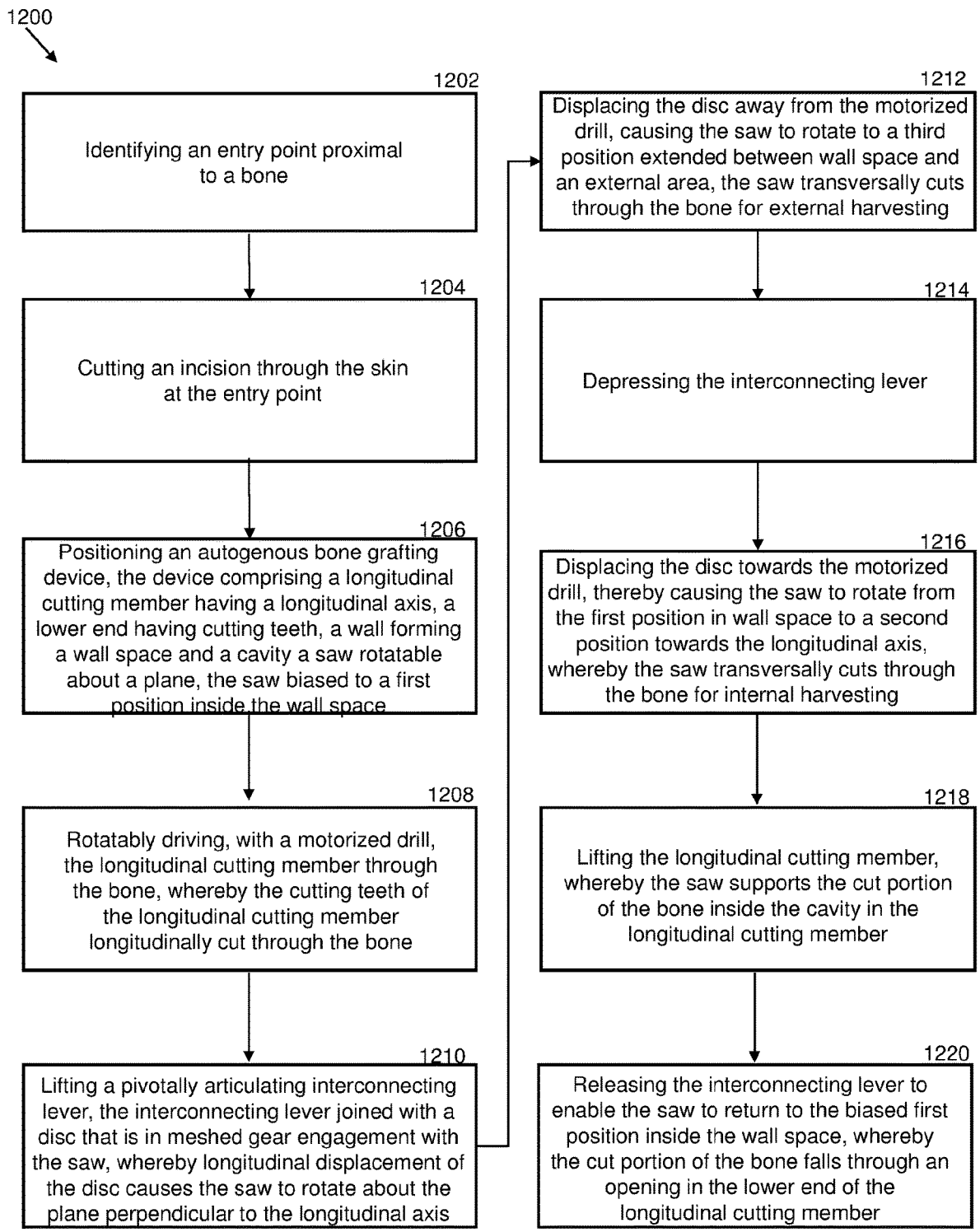
FIG. 12 illustrates a flowchart diagram of an exemplary method for autogenous bone grafting, in accordance with an embodiment of the present invention.

FIG. 12 illustrates a flowchart diagram of an exemplary method 1200 for autogenous bone grafting. The method 1200 may include an initial Step 1202 of identifying an entry point proximal to a bone. The method 1200 may further comprise a Step 1204 of cutting an incision through the skin at the entry point. The method 1200 is operational in any portion of the body that supports bone structure for autogenous bone grafting.

A Step 1206 includes positioning an autogenous bone grafting device proximal to the entry point, the device comprising a longitudinal cutting member defined by a central longitudinal axis, a lower end having cutting teeth, a wall forming a wall space and a cavity, the device further comprising a saw rotatable about a plane perpendicular to the longitudinal axis, the saw being biased to a first position inside the wall space.

In some embodiments, a Step 1208 comprises rotatably driving, with a motorized drill, the longitudinal cutting member through the bone, whereby the cutting teeth of the longitudinal cutting member longitudinally cut through the bone. After having identified an entry point onto the patient's pelvis, and had made an incision through the skin, the operator switches on the motor of the device 100, and the longitudinal cutting member 104 begins to spin in the clockwise direction at a suitable speed.

At this point, the cutting teeth 122 forming at the lower end 108 of the longitudinal cutting member 104 first contact the pelvic bone 212 (usually at the top rim of the iliac crest), and begins to penetrate into the pelvis. After the longitudinal cutting member 104 has entered a depth of 10 mm, as indicated on an optional gauge scale 170 at the side of the longitudinal cutting member 104

A Step 1210 includes lifting a pivotally articulating interconnecting lever, the interconnecting lever joined with a disc that is in meshed gear engagement with the saw, whereby longitudinal displacement of the disc causes the saw to rotate about the plane perpendicular to the longitudinal axis.

As shown in FIG. 11, and whilst the longitudinal cutting member 104 continues to spin at a high speed, the operator depresses the handle 162 with a first finger to maximum extent to move the saw 140 from the first position 206 as shown in FIG. 2A to a second position 208 as shown in FIG. 2C. This is possible through a Step 1212, which includes displacing the disc away from the motorized drill, causing the saw to rotate to a third position partially extended between the wall space and an external area outside the cavity of the longitudinal cutting member, whereby the saw transversally cuts through the bone for external harvesting. When this is achieved, the base of the bone block 214 is fully sectioned, and separated from the pelvis and resides inside the longitudinal cutting member 104 within the cavity 112 of the longitudinal cutting member 104.

In some embodiments, a Step 1214 comprises depressing the interconnecting lever. In some embodiments, a Step 1216 may include displacing the disc towards the motorized drill, thereby causing the saw to rotate from the first position in the wall space to a second position towards the longitudinal axis running through the longitudinal cutting member, whereby the saw transversally cuts through the bone for internal harvesting. A Step 1218 comprises lifting the longitudinal cutting member, whereby the saw supports the cut portion of the bone inside the cavity in the longitudinal cutting member.

A final Step 1220 includes releasing the interconnecting lever to enable the saw to return to the biased first position inside the wall space, whereby the cut portion of the bone falls through an opening in the lower end of the longitudinal cutting member. The operator keeps the first finger on the handle 162 in order to maintain the saw 140 at this particular third position 210, as shown in FIG. 3C, and withdraws the entire device 100 and longitudinal cutting member 104 out of the pelvis. Next the operator switches off the motor, and lifts the handle 162 up towards its original position for the saw 140 to retract to be concealed within the wall 118 as shown in FIG. 3A, and the bone block 214 readily drops onto the operator's hand, as shown in FIG. 10.

Although the process-flow diagrams show a specific order of executing the process steps, the order of executing the steps may be changed relative to the order shown in certain embodiments. Also, two or more blocks shown in succession may be executed concurrently or with partial concurrence in some embodiments. Certain steps may also be omitted from the process-flow diagrams for the sake of brevity. In some embodiments, some or all the process steps shown in the process-flow diagrams can be combined into a single process.

And to further describe the use of the device 100 in practice, let us assume that an operator decides to separate the top external end of the femur (thigh bone) with the view to remove the femoral head for a hip replacement surgery, the device 100 which is calibrated for this purpose will, after the longitudinal cutting member 104 has reached a suitable depth within the femur bone, after firstly entering this long bone of the thigh from the top of it.

Figure 7:
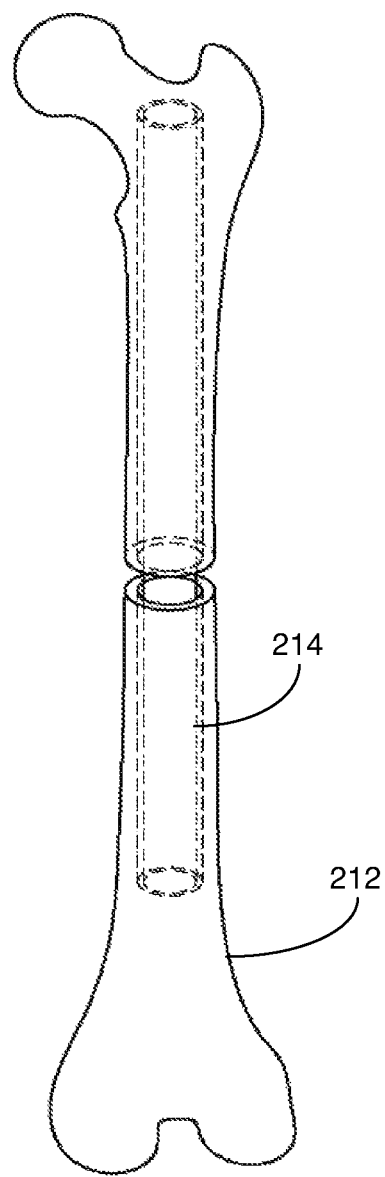
FIG. 7 illustrates a perspective view of process of sectioning and separating surrounding bone when a third position of the saw is effected by the device shown in FIG. 1; separating the upper outer portion of the femur bone and the femoral head is an example case for hip replacement surgery, in accordance with an embodiment of the present invention.

The operator this time will lift up the handle 162 with a first finger (lifting it upwards instead of depressing it), and this will cause a clockwise rotation of the disc 134 which will in turn cause a clockwise rotation of the saw gear 146, and the rod 128 and thus the saw 140 to move outside of the longitudinal cutting member 104 and into the surrounding bone tissues, along a horizontal plane 202. In the case of the cylindrical femur bone 212 (circular in cross-sectional view with a typical diameter of 1" thickness). At this juncture, the saw 140 advances to a third position 210 will section a portion of the outer shell of the femur bone whilst the longitudinal cutting member 104 has already separated the medulla of the femur bone from its outer shell cortex of cortical bone, as shown in FIG. 7.

After this is achieved, the operator uses the first finger to depress the handle 162 of the interconnecting lever 158 to an exact extent back to the first position 206 as shown in FIG. 3A, and proceeds to retrieve the longitudinal cutting member 104 and the entire device out of the femur bone 212. Now that the top of the femur bone shell is clearly separated, it is a simple task of removing this (degenerated) upper portion of the femur from the rest of the femur using conventional surgical methods, and intended to be replaced with an artificial hip device 100.

In yet another embodiment of the device 100, a hollow longitudinal cutting member 104 (trephine) is operatively connected to a motorized drill 102 and includes several components. In its most a basic form, it consists of a main longitudinal cutting member 104, a disc 134 above the longitudinal cutting member 104, at least one saw 140, a saw gear 146, a rod 128, and at least one saw 140.

The device 100 has an actuating means for actuating movement of the saw 140 relative to the longitudinal cutting member 104 between a first position 206 in which said saw 140 is clear of the opening 110 at the lower end 108 of the longitudinal cutting member 104 to permit the drilled bone portion to pass through the opening 110 into the cavity 112 and a second position 208 in which the saw 140 restricts passage of part of the lower open end of the longitudinal cutting member 104, or between the first position 206 and a third position 210 in which the saw 140 extends outside of the longitudinal cutting member 104 to move across a plane 202 which is substantially perpendicular to said rod axis 204. The actuating means could be a disc 134 which is a large and thick diameter ring with a circular hole 138 at its center. The disc 134 is placed close to the top surface of the longitudinal cutting member 104. The drill shaft 126 extends through the circular hole 138 of the disc 134 at the center of the disc 134.

The disc 134 is placed around a drill shaft 126 with a helical member 152 in engagement which controls the rotation of the disc 134 as it moves up and down along the drill shaft 126. The direction of the helical member 152 is calibrated in such a way that as the disc 134 is moved downwards along this drill shaft 126, it is effected to rotate clockwise. Conversely, as the disc 134 is moved upwards along this drill shaft 126, it is effected to rotate anticlockwise. The disc 134 can move relative to the drill shaft 126, including rotating about the drill shaft 126 about a common central longitudinal axis 200, and moving up and down along the drill shaft 126.

The disc 134 usually rests on a cutting member shoulder 124 which is of an equal diameter as the disc 134. The outer rim surface of the disc 134 is smooth, but a portion of its inner rim surface is serrated with disc teeth 136. The disc teeth 136 are in meshed engagement with the saw gear 146 for rotating the saw gear 146.

The disc 134 is in mesh engagement with a saw gear 146 such that the disc teeth 136 of the inner rim surface of the disc 134 are in constant engagement with saw gear 146 of the outer rim surface of the saw gear 146. Such an arrangement controls the rotational movement and position of the saw 140, to be discussed below.

A drill shaft 126 is provided at an upper end 106 of the longitudinal cutting member 104. The drill shaft 126 has threads for loosely engaging with the disc 134. The helical member 152 may include a calibrated screw-threading, which may be only a single threading, or only just a few prominent threads suffices. The helical member 152 never screws tightly, it is merely a pathway guide, or a track.

The device 100 includes a longitudinal cutting member 104. In some embodiments, venting holes 174 may be formed through the longitudinal cutting member 104 to allow saline water coolants to enter a drill cavity 112 in the longitudinal cutting member 104 during operation. This helps keeps components, such as a bone stud cool and flushes away debris. After operation, the harvested bone 212 is contained within the drill cavity 112.

The saw gear 146 is fixed to the top end 130 of the rod 128, and directly above the opening 110 of a drill tunnel 176 which runs through both the longitudinal cutting member 104 and the cutting member shoulder 124.

As discussed above, the outer surface of the saw gear 146 has vertical serration of saw gear 146 in constant contact and engagement with vertical serration of disc teeth 136 that form along the inner surface of the rim of the disc 134. The top of the rod 128 is fixed to the saw gear 146 and these two embodiments are fabricated in one casting.

Rotation of the disc 134 relative to the longitudinal cutting member 104 about the longitudinal axis 200 will bring about rotation of the saw gear 146 through the constant contact and engagement between the saw teeth 148 of the saw gear 146, and the disc teeth 136.

The disc 134 may be moved along the drill shaft 126 guided by a helical member 152 along the drill shaft 126 towards and away from the cutting member shoulder 124, to bring about movement on the part of the saw gear 146. As discussed above, the helical member 152 between the disc 134 and the drill shaft 126 is in loose engagement. The effect is that the disc 134 can only move upwards or downwards along the drill shaft 126 vertically, but cannot move horizontally relative to the drill shaft 126.

When the disc 134 is moved upwards along the drill shaft 126, the disc 134 and the saw gear 146 are together rotated anticlockwise and at the same time this rotates the rod 128 and the saw 140 anticlockwise to move the saw 140 towards the center point of the open longitudinal end of the drill cavity 112.

When the disc 134 is moved downwards along the drill shaft 126, the disc 134 and the saw gear 146 are together rotated clockwise and at the same time this rotates the rod 128 and the saw 140 away from the center point of the open longitudinal end of the drill cavity 112.

In particular, the respective saw gear 146 of the disc 134 and the disc teeth 136 of the saw gear 146 are fixed-engaged lengthwise along and relative to each other to cause a relative rotational movement between the disc 134 and the saw gear 146.

The rod 128 is defined by a top end 130 and a bottom end 132. The rod 128 may include a long rectangular rod 128 which passes down within the longitudinal cutting member 104 and through the drill tunnel. An end of the saw 140 is fixedly connected close to the bottom end 132 of the rod 128.

In another embodiment according to the invention, the rod 128 can be circular in cross-section and not necessarily rectangular. Similarly, the drill tunnel 176 can be circular in cross-section and not necessarily rectangular. However, the drill tunnel 176 is immaterial, and in manufacturing reality, the drill tunnel 176 could be omitted. For example, the rod 128 can rest in an open vertical window 116 for accommodating the rod 128 pivoting at the lower end 108, piercing through a hole 138, and the upper end 106 resides in an indented portion of the drill surface, and secured in place as the disc 134 assembles down over the saw gear 146, to contain it like snug-fit.

The top end 130 of the rod 128 is fixedly connected with the saw gear 146, and passes outside of the longitudinal cutting member 104 at the end of the longitudinal cutting member 104 to be connected at the lower end 108 with the saw 140. Rotation of the saw gear 146 affects rotation of the saw 140. The rod 128 functions also as a hinge 168 for the rotational movement of the saw 140, since the rod 128 is connected perpendicularly to one end of the saw 140. Thus, when the rod 128 is positioned vertically, the saw 140 lies flat. The rod 128 passes through and beyond the saw 140 and finishes as a sharp point, which rests on a hidden platform provided by a drill end in order to contain the rod 128. The rod 128 essentially acts as a spindle. The top of the rod 128 is fixedly connected to the center of the saw gear 146.

The saw 140 has a base end 142 and a tip end 144, and is pivotable relative to the longitudinal cutting member 104 about a rod axis 204 of the rod 128 (which is parallel to the central longitudinal axis 200 of the longitudinal cutting member 104) to open and partially close a lower open end of the drill cavity 112 of the longitudinal cutting member 104. The rod 128 is connected to a flat surface of the base end 142 of the saw 140 at 90°. The flat surface of the saw 140 is parallel to the horizontal, and cutting teeth 122 of the face of the saw 140 towards and away from the lower open end of the longitudinal cutting member 104. In one non-limiting embodiment, the rod 128 and the saw 140 can be fabricated as a one cast component.

The incorporation of the saw 140 is important to this invention because it serves not only to section the end of the bone stud, at any chosen cut-off point, but also it subsequently serves as a floor base of the drill cavity 112, fully containing the bone block 214 within, to provide support as the bone block 214 (stud) is lifted out from its original site naturally attached to the native bone 212, completely concealed in the drill cavity 112 of the longitudinal cutting member 104.

When the disc 134 is positioned relatively closer to the cutting member shoulder 124, the saw 140 is totally clear of the open end of the drill cavity 112 of the longitudinal cutting member 104. When the disc 134 is rotated anticlockwise about its central longitudinal axis 200 relative to the longitudinal cutting member 104 away from the cutting member shoulder 124, the saw gear 146, with the rod 128 with which it is fixedly engaged, is caused to rotate about the rod axis 204 of the rod 128, to bring about corresponding anticlockwise movement of the saw 140 to a second position 208 in which the saw 140 restricts passage of part of the open longitudinal end of the drill cavity 112 of the longitudinal cutting member 104.

It is preferable when aiming for the bone harvesting process to take place, to arrange the components such that when the saw 140 restricts passage of part of the open longitudinal end of the drill cavity 112 of the longitudinal cutting member 104, it blocks the center point of the open longitudinal end of the drill cavity 112, as in the case of FIG. 3C.

In operation of the device 100, this downward drilling creates a circular block of bone 212, whose length is determined by the depth of this drilling. It can be seen that the device 100 allows the user to harvest a block of bone 212 of up to any pre-determined length when the longitudinal cutting member 104 has drilled and reached a pre-determined depth into the bone 212 which is substantially equal to the length of the drill cavity 112.

The drill shaft 126 of the hollow longitudinal cutting member 104 is directly connected to a motorized drill 102 and the operation is selectively controlled by an interconnecting lever 158 defined by an actuation end 160 and a cap end 164. The interconnecting lever 158 is configured to pivot about a hinge 168 on the motorized drill 102. The actuation end 160 of the interconnecting lever 158 terminates at a U-shaped connecting member 166 which rests within a recess 156 space between the disc cap 154 and the top surface of the disc 134, around an isthmus connecting the disc 134 to the disc cap 154.

In this manner, the longitudinal cutting member 104, disc 134 and disc cap 154 are spinning at high speed, while the U-shaped connecting member 166 at the actuation end 160 is at rest around the isthmus and is ready to control the up and down movements of the disc 134 along the shaft 24, via either lifting or depressing the handle 162 of the interconnecting lever 158 at the extreme end of the interconnecting lever 158, relatively and respectively.

The interconnecting lever 158 could be a fork, U-shaped connecting member 166 on either side of the neck of the button, or could be a horizontal groove to slot the U-shaped connecting member 166 into. The idea is to allow the handle 162 and the disc 134 to spin freely at high speed, while still allowing the U-shaped connecting member 166 ensures its vertical position at all times, securing this aspect.

During the entire procedure, the longitudinal cutting member 104 spins, at about 2,000 rpm, the operator removes the finger from the handle 162 of the interconnecting lever 158, and the device 100 will automatically reset to default status, factory-set position, thanks to the spring 150 which biases the disc 134 suitably, specifically for this very aim, so that as long as the operator doesn't touch the interconnecting lever 158, the U-shaped connecting member 166 will passively retreat to reside naturally at a default horizontal level (point zero 0 on the gauge scale 170), at which point no cutting occurs, and the saw 140 is in first position 206, passively hidden within a wall space 120 in the wall 118, and allows the longitudinal cutting member 104 to advance freely in and out of the body as any ordinary hollow drill (trephine).

Only when the operator either presses down or lifts up the interconnecting lever 158, and keeping the finger actively on the handle 162, then the saw 140 respectively moves across a plane 202 substantially perpendicular to the rod axis 204, and to exactly proportional extents according to the precise amount of pressure the finger exerts.

Therefore, the U-shaped connecting member 166 can toggle the disc 134 upwards and downwards as the operator wants at any time during the spinning, which in turn (via the engaged disc teeth 136 internal surface of the disc 134) will turn the saw gear 146 accordingly, and in turn also toggle the rod 128 to turn the saw 140 in and out of the lumen, inwards (second position 208) or outwards (third position 210) across the plane 202 (horizontal plane 202) which is substantially perpendicular to the rod axis 204.

The center of the interconnecting lever 158 pivots via a pivoting hinge 168 located on the side surface of the motorized drill 102. The near end of the interconnecting lever 158 finishes as a U-shaped connecting member 166 to rest between the disc cap 154 and the disc 134 at a recess 156 space (for example the isthmus), and the other end of the interconnecting lever 158 finishes as a free end, incorporating a handle 162, for the surgeon's finger to manipulate.

The interconnecting lever 158 can be depressed downwardly, or lifted upwardly to control the movement of the saw 140 during the operation, via all of the intermediary connected components of the entire device 100, namely, the U-shaped connecting member 166 resting at the isthmus. The isthmus positioned on the top surface of the disc 134, the disc 134 is in mesh engagement with the saw gear 146 which is located at the top end 130 of the rod 128, and the saw 140 located at the lower end 108 of the rod 128.

Additionally, the interconnecting lever 158 can be readily retracted back to resume the factory default position "at any time" during the procedure to correspondingly retract the saw 140 also to the first position 206 (reset), and at that point, the saw 140 is controllable to either be retracted out of the longitudinal cutting member 104, or can be chosen to be proceeded onwards (carry on) for to conduct additional cutting into bone 212, as the operator optionally chooses.

If the interconnecting lever 158 is moved downwards to the factory set maximum limit during the procedure, for the second position 208, the tip end 144 of the saw 140 advances across a plane 202 which is perpendicular to said rod axis 204 to reach the center point (central axis) of the lumen, and thus this translates to the cut bone block 214 inside of the device 100 being completely separated from the native bone 212 and is ready to be harvested by the device 100 upon withdraw. This can be regarded as an "Internal Harvesting of Bone Sample".

In another instance, if the interconnecting lever 158 is moved upwards to the factory set maximum limit during the procedure, for the third position 210, the tip of the saw 140 will have moved across the plane 202 which is perpendicular to rod axis 204 to reach a suitable position outside of the device 100 and into the surrounding bone and slightly beyond into the surrounding soft tissues, and thus this translates to the bone 212 (bone shell) outside of the longitudinal cutting member 104 being completely separated from the native bone 212. Assuming that the surrounding soft tissues and muscular attachments to the external surfaces of the intended bone sample have also been dissected away beforehand, then this external bone portion is ready to be harvested by the device upon withdraw. This can be regarded as "External Harvesting of Bone Sample".

In FIG. 2A, the disc teeth 136 are wide diameter along the inner surface of the disc 134 (thus not restricting the wheel as the disc turns), and the disc 134 should be able to effect turning of two wheels at opposite ends to each other, if the device 100 contains two sets of saws, or a plurality of saws. The disc teeth 136 are not to surround the saw gear 146, but merely point-contacts the saw gear 146 at the edge, at all times. For the disc 134, after it slots down onto the device 100, the inner mesh portion could be slot in from outside and 2 or 3 mini screws from above secures it into place. And for the rod 128, or drill tunnel 176 or open vertical slot that could be of rectangular or circular in cross-section.

With reference to FIG. 2C, in one embodiment according to the invention, the other end of the interconnecting lever 158 is simply a U-shaped connecting member 166 which resides passively and embraces around the recess 156 space that forms in the disc 134, or slots into a specific groove for it; as the entire longitudinal cutting member 104 spins rapidly. The U-shaped connecting member 166 is stationary, but the U-shaped connecting member 166 is merely there to lift up or to depress the disc 134 in the vertical plane 202. In fact the U-shaped connecting member 166 could be just a single U-shaped connecting member 166 on one side to lift or to depress the disc 134.

The vertical position of the disc 134 along the drill shaft 126 is crucial, because in-effect it determines the rotation of the saw 140 and to what relative extents or degree of rotation, or the direction from the first position 206 to the second position 208, or the direction from the first position 206 to the third position 210.

Also, if the interconnecting lever 158 is fixated in a position, it actually in-effect locks the saw 140 in that relative position (something like a lock control). As for the saw gear 146, the mesh is vertical grooves for engaging with the inner surface vertical mesh of the disc 134, but at the same time also allowing for the disc 134 to move freely up and down alongside it.

Only the outer edge of the saw gear 146 needs to be engaged with the disc 134 at all times. Therefore, when the device 100 is spinning at high speed, together with the disc 134, the interconnecting lever 158 actually (in-effect) locks the disc 134 at that height and nothing is loosely flying about. This in-turn also locks the saw 140, namely the interconnecting lever 158 functioning like a lock control, as discussed above.

The mechanism in function is such that as the main body of the device 100, the hollow longitudinal cutting member 104 is driven by the attached motorized drill 102, to spin in a clockwise direction, and is spinning at high speed, the operator enters the device 100 directly into the patient's bone 212, usually into the pelvis, and as soon as the device 100 penetrates inwards to a desired depth, the operator depresses the handle 162 at the end of the interconnecting lever 158 that in effect lifts the disc 134 upwards, which is effected to rotate anticlockwise guided by a helical member 152 on the drill shaft 126, and also engaged with the mechanical saw gear 146 which also rotates anticlockwise in effect to rotate the saw 140 at the bottom of the longitudinal cutting member 104 (via the rod 128), moving horizontally across the plane 202 until it reaches a limit when the interconnecting lever 158 cannot be depressed any further, and coincides with the tip of the saw 140 reaching the very center of the cavity 112 in the longitudinal axis 200 of the longitudinal cutting member 104, as shown in FIG. 3C.

In this way, the block of bone 212 which now occupies the space inside the hollow cavity 112 of the device 100 is sectioned by the saw 140, to be separated from the rest of the pelvis, isolated and captured, and upon withdrawal of the device 100, and it is harvested.

In terms of the mechanics, the interconnecting lever 158 allows full control of the saw 140 of the device 100 for the operation. As the device 100 is speedily spinning inside the bone 212 (pelvis), at any time during for any given depth reached, the operator can depress the interconnecting lever 158 to effectively rotate the saw 140 inwards towards the center of the cavity 112 against the bone 212, sectioning it during this action.

The interconnecting lever 158 is spring loaded with a biasing means. The biasing means could be a built-in spring 150 that biases to push downwards the U-shaped connecting member 166 of the interconnecting lever 158 on the U-shaped connecting member 166 for the handle 162 to stay in the top position at rest, and this maintains a downward force on U-shaped connecting member 166 and also the disc 134 (pressing it downwards) so as to ensure that the saw 140 is within the wall 118 at rest. This is important during the downwards drilling phase to avoid the saw 140 from accidentally intruding prematurely into the cavity 112 and obstructing the entire longitudinal cutting member 104 from proceeding downwards into the body.

Therefore at any moment that the operator does not contact the handle 162 of the interconnecting lever 158, the spring 150 pushes down on the disc cap 154 which in turn pushes down of the U-shaped connecting member 166 of the interconnecting lever 158, which in effect lifts up the handle 162 automatically upwards to its uppermost top limit position, and the saw 140 is safe and securely retracted into the wall space 120 in the wall 118 and discretely hidden (out of the way) as shown in FIG. 3A. This is almost like a locked position provided by the built-in spring 150 component between the motorized drill 102 and the top of the disc cap 154 positioned around the drill shaft 126.

The interconnecting lever 158 (handle 162 and via pivot to move U-shaped connecting member 166) in-effect determines and directly controls the degree and extent of the saw 140 to cut smoothly into the bone 212 across the horizontal plane 202 perpendicular to the rod axis 204, inside the lumen.

The interconnecting lever 158 independently controls the amount of cutting across a plane 202 which is substantially perpendicular to the rod axis 204 as effected by the saw 140, whether partially, and to exacting extents as the operator desires, or to maximum extents for the purposes of harvesting solid bone samples (via all the associated intermediary gear components of the device 100, interconnected between the interconnecting lever 158 and the saw 140).

Figure 6:
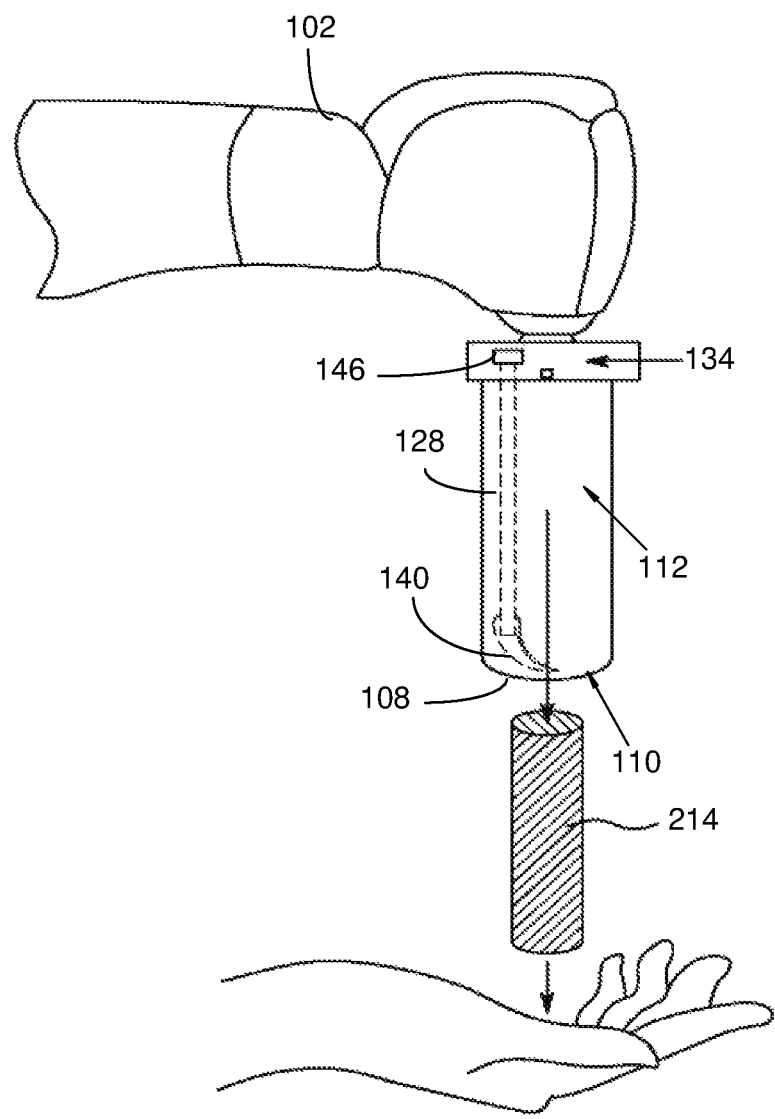
FIG. 6 illustrates a perspective view of a full cylindrical block of bone harvested without division, by the device shown in FIG. 1, in accordance with an embodiment of the present invention.

With reference to FIG. 6, during the drilling down process of the device 100 into the body, pressing the interconnecting lever 158 a bit will make a groove around the bone block 214. The operator releases the finger to release the interconnecting lever 158 to its default level, and drill down the device 100 into the body a bit more, and presses the interconnecting lever 158 a bit to make another groove, and so on. As results, a series of grooves along the length of the bone block 214 sample are made, and then finally when the drill reaches its maximum depth.

The operator presses the interconnecting lever 158 fully, to its maximum limit, and completely separates the entire bone block 214 from the base connection (native bone 212) isolating the bone 212 with a series of grooves created along its length, and, by maintaining the finger on the handle 162 fully, the operator harvests the bone 214 upon withdraw of the longitudinal cutting member 104, and taken out of the body encapsulating the bone block 214 sample.

And the saw 140, whether a single or pair of such saws working simultaneously for synergy, are also readily retractable back to the default position (facilitated by the above spring 150, and this versatility allows for the entire contraction to be reset and for it to be entered furthermore deeper into the body to do another sectioning at a deeper portion, for another cross-cutting.

As far as the operator is concerned, he/she controls the inward (or outward) across-cutting of the saw 140 at the tip of the device 100 simply by pressing down (or uplifting) to trigger the interconnecting lever 158 at the handle 162, at any time during the device 100 is inside the body and spinning at high speed.

Therefore, between the handle 162 and the saw 140 are simply interconnecting gadgetry components that makes it works. Therefore, it's a device 100 that uniquely allows for the control of the saw 140 to dig into the bone 212, to certain extents or all desired extents, and also outwards cutting, and remains retractable back to the first position 206 well within the wall 118 (discreetly hidden), simply by manipulating the interconnecting lever 158 arm accordingly.

The calibration is such that if the handle 162 of the interconnecting lever 158 is depressed to anywhere halfway between its first position 206 at the upper limit position; whereby the saw 140 resides hidden within the wall space 120, as shown in FIG. 3A, and the second position 208 at lowest limit position; whereby the tip end 144 of the saw 140 is rotated to swing 90° anticlockwise to reach the longitudinal axis 200 of the longitudinal cutting member 104, as shown in FIG. 3C, with the interconnecting lever 158 in this midway position, the saw 140 only sections the bone 212 within the cavity 112 space only somewhere halfway through, correspondingly, and not completely, as shown in FIG. 3B. This fractional sectioning is a main feature of this device 100 allowing for full control and precision offered by this scientific instrument. FIG. 3A can be referred to as a first position 206. FIG. 3B shows the saw moving towards the second position 208. FIG. 3C shows the saw at the second position 208.

During this process, after the handle 162 of the interconnecting lever 158 is depressed slightly to effect either partial or completely for either partial of full sectioning across the captioned bone 212, whilst the longitudinal cutting member 104 is still spinning clockwise at high speed inside the patient, the interconnecting lever 158 can be readily lifted again upwards to retract the saw 140 away from the bone 212, and/or completely back into the wall 118 where it is discreetly hidden again, and no longer to intrude the cavity 112 of the longitudinal cutting member 104, so as not to obstruct the up and down free movement of the longitudinal cutting member 104.

The full control of the inward towards the center, and/or outward movement of the saw 140, even beyond the boundaries of the longitudinal cutting member 104 to extend to the surrounding tissues, and in variable amounts, of the saw 140 across the horizontal plane 202 during its spinning inside of the human body, and the saw 140 is also subsequently retractable to its original position, is a unique feature of this device 100.

The gauge scale 170 may have millimeter markings alongside the handle 162 of the device 100 can be included to serve to precisely indicate the depth of saw cutting into the bone 212 during the active process in real time. At the same time, there also exists a vertical gauge 172 with millimeter markings on the outside and alongside the longitudinal cutting member 104 which serves to indicate the depth entered by the longitudinal cutting member 104 into the body (pelvis, sacrum, ribs, or other suitable bones of the human body). In this way, this device 100 offers unprecedented precision for the extraction of bone 212, whether for therapeutic purposes (bone grafting) or for bone sample analysis, or also for harvesting bone marrow for analysis in metabolic and renal medical diseases.

With reference to FIG. 11, with the precision requirements for bone grafting, the gauge scale 170 and the vertical gauge 172 provide factory-set millimeter markings. These markings enable the surgeon to drill down into the body to a depth of about 2 mm, and then depress the interconnecting lever 158, to create an across-cut groove into the bone block 214 inside the drill just 1 mm indentation groove, lift the lever 158 to default, and then drill down another 2 mm to make another across-cut groove of 1 mm indentation. Such grooves can be cut in such a manner all the way down the full length of the longitudinal cutting member 104.

At the final groove, the lever 158 can be fully depressed when the saw 140 digs across right through to the center point (central axis of the lumen) and completely section the block, and keeping the lever 158 depressed at that point, withdraw the entire device 100 out of the body with a full bone block 214 inside, with a series of 1 mm indented grooves along its length at 2 mm intervals. This is a demonstration of the control this instrument device 100 offers, and this high level of precision and control is unprecedented.

A further variation version of this device 100 design is that, in addition to the functions already mentioned, the device 100 can be modified whereby the handle 162 of the interconnecting lever 158 can be lifted up even further, beyond the pre-existing upper limit, and via the handle 162, this end of the interconnecting lever 158 is allowed to be lifted up beyond this previous range. As this end of the interconnecting lever 158 is lifted further upwards, this will consequently result in pushing down on the disc 134 even further downwards in order to rotate the disc 134 clockwise and to rotate the saw 140 clockwise, this time the saw 140 is moved outwards (as opposed to inwards, as previously described so far) and away from the longitudinal cutting member 104 as shown in FIG. 6, this can be referred to as a third position 210, across the plane 202 perpendicular to the longitudinal axis 200.

When this happens during the spinning of the device 100 inside the bone 212, this will cause a cutting, or sectioning of the surrounding bone 212 outside of the longitudinal cutting member 104 and the device 100. When this cutting is achieved, the handle 162 is pressed down again by the operating surgeon to the original preset position (which can be referred to as a first position 206), in order to retract the saw 140 back into the wall 118, and allows the entire device 100 to be withdrawn and removed from the body, after this saw sectioning has been already achieved.

The new feature offered by this device 100 is the possibility of 'external bone harvesting' whereby if the device 100 is entered into the femur (top of the leg bone). The saw 140 is effected via the lever arm (through the intermediary components such as the interconnecting lever 158) to slide outwards of the device 100 (into the surrounding tissues) across the horizontal plane 202 perpendicular to the rod axis 204; and to cut through the outer thickness of the femur bone (cortical outer layer), and just beyond it but not cutting too much into the thigh muscles.

The purpose is merely to detach the degenerated upper portion of the femur plus associated head of the femur (which is to be subsequently replaced by a hip replacement titanium device). This control of the degree of cutting sections the outer shell of the top portion of the femur, but not too extruding that would otherwise also cut through the leg muscles. Then the saw 140 is retracted to default position, and the device 100 can be retrieved out of the femur bone, leaving a 'freed' upper portion of the femur ready for detachment by the surgeon. This avoids too much external tissue dissection for the endeavor.

In orthopedics, this feature can be optionally applicable for the removal of the degenerated head of the femur bone 212 (femoral head), as shown in FIG. 7, or thigh bone 212, by inserting the device 100 longitudinally from the top of the femur within the 1 inch diameter of the femur, inserted to a suitable depth for this sectioning to take place. (Some superficial muscle detachment may be necessary for the subsequent removal of the femoral head after this saw 140 sectioning had created its freedom).

To further describe the use of the device 100 in practice, let us assume that an operator would like to harvest a bone block 214 of a length of 10 mm. After having identified an entry point onto the patient's pelvis, and had made an incision through the skin, the operator switches on the motor of the device 100, and the dill body 32 begins to spin in the clockwise direction at a suitable speed. The cutting teeth 122 forming at the lower end 108 of the dill body 32 first contact the pelvic bone 212 (usually at the top rim of the iliac crest), and begins to penetrate into the pelvis.

After the longitudinal cutting member 104 has entered a depth of 10 mm, as indicated on an optional scale (the vertical gauge 172) at the side of the longitudinal cutting member 104, as shown in FIG. 11, and whilst the longitudinal cutting member 104 continues to spin at a high speed, the operator depresses the handle 162 with a first finger to maximum extent to move the saw 140 (cross-saw 140) from a first position 206 as shown in FIG. 3A to a second position 208 as shown in FIG. 3B.

When this is achieved, the base of the bone block 214 is fully sectioned, and separated from the pelvis and resides inside the longitudinal cutting member 104 within the cavity 112. The operator keeps the first finger on the handle 162 in order to maintain the saw 140 at this particular third position 210, as shown in FIG. 3C, and withdraws the entire device 100 and longitudinal cutting member 104 out of the pelvis. Next the operator switches off the motor, and lifts the handle 162 up towards its original position for the saw 140 to retract to be concealed within the wall 118 as shown in FIG. 3A. Finally, the bone block 214 readily drops onto the operator's hand (FIG. 10).

And to further describe the use of the device 100 in practice, let us assume that an operator decides to separate the top external end of the femur (thigh bone) with the view to remove the femoral head for a hip replacement surgery, the device 100 which is calibrated for this purpose will, after the longitudinal cutting member 104 has reached a suitable depth within the femur bone 212, after firstly entering this long bone 212 of the thigh from the top of it; the operator this time will lift up the handle 162 with a first finger (lifting it upwards instead of depressing it).

This results in a clockwise rotation of the disc 134 which will in turn cause a clockwise rotation of the saw gear 146, and the rod 128 and thus the saw 140 to move outside of the longitudinal cutting member 104 and into the surrounding bone tissues, along a horizontal plane 202. In the case of the cylindrical femur bone 212 (circular in cross-sectional view with a typical diameter of 1" thickness), the saw 140 now moved to a third position 210 will section a portion of the outer shell of the femur bone 212 whilst the longitudinal cutting member 104 has already separated the medulla of the femur bone 212 from its outer shell cortex of cortical bone (FIG. 7).

After this is achieved, the operator uses the first finger to depress the handle 162 of the interconnecting lever 158 to an exact extent back to the first position 206 as shown in FIG. 3A, and proceeds to retrieve the longitudinal cutting member 104 and the entire device out of the femur bone. Now that the top of the femur bone shell is clearly separated, it is a simple task of removing this (degenerated) upper portion of the femur from the rest of the femur using conventional surgical methods, and intended to be replaced with an artificial hip device. In addition to bone harvesting from the human body, the device 100 according to the present invention can be used as well for other materials in other industries, including for Bone Marrow harvesting from the human body.

It should also be understood that certain features of the invention, which are, for clarity, described in the context of separate embodiments, may be provided in combination in a single embodiment. Conversely, various features of the invention which are, for brevity, described in the context of a single embodiment, may also be provided separately or in any appropriate sub-combinations.

These and other advantages of the invention will be further understood and appreciated by those skilled in the art by reference to the following written specification, claims and appended drawings.

Because many modifications, variations, and changes in detail can be made to the described preferred embodiments of the invention, it is intended that all matters in the foregoing description and shown in the accompanying drawings be interpreted as illustrative and not in a limiting sense. Thus, the scope of the invention should be determined by the appended claims and their legal equivalence.

What is claimed is:

1. A device for autogenous bone grafting, the device comprising:
    a longitudinal cutting member being defined by an upper end and a lower end forming an opening to a cavity, the longitudinal cutting member further being defined by a wall forming a wall space, the lower end of the longitudinal cutting member comprising a plurality of cutting teeth, the longitudinal cutting member being rotatable about a longitudinal axis;
    a drill shaft joined with the upper end of the longitudinal cutting member, the drill shaft being substantially aligned with the longitudinal axis of the longitudinal cutting member;
    a motorized drill joined with the drill shaft, the motorized drill rotatably driving the drill shaft and the longitudinal cutting member,
    whereby the cutting teeth of the longitudinal cutting member are operable to enable longitudinal cutting through a bone;

a rod being defined by a top end and a bottom end, the rod being rotatable about a pivoting axis, the pivoting axis being disposed in a spaced-apart, parallel relationship with the longitudinal axis;

at least one saw joined with the bottom end of the rod, proximal to the lower end of the longitudinal cutting member, the saw being rotatable along a plane perpendicular to the pivoting axis, whereby the saw is operable to enable transversal cutting through the bone whereby the saw rotatably articulates along the plane between a first position substantially inside the wall space of the wall, and a second position extended between the wall and the longitudinal axis of the longitudinal cutting member;

whereby the saw rotatably articulates along the plane between the first position and a third position partially extended between the wall space and an external area outside the cavity of the longitudinal cutting member;

a saw gear defined by a plurality of saw teeth, the saw gear joined with the top end of the rod;

a disc being in engagement with the drill shaft, the disc being configured to advance along the drill shaft towards the motorized drill, the disc further being configured to advance along the drill shaft away from the motorized drill, the disc comprising disc teeth disposed in meshed engagement with the saw teeth;

a spring disposed around the drill shaft, the spring biasing the disc away from the motorized drill to the first position;

a helical member disposed in the hole of the disc, the helical member being in engagement with the disc and the drill shaft, whereby the helical member causes the disc to rotate clockwise while advancing towards the motorized drill, whereby the helical member causes the disc to rotate counterclockwise while advancing away from the motorized drill, whereby when the disc advances along the drill shaft towards the motorized drill, the disc teeth rotate against the saw teeth, causing the saw gear to rotate in an anticlockwise direction, causing the rod and the saw to rotate in the anticlockwise direction to the second position, whereby when the disc advances along the drill shaft away from the motorized drill, the disc teeth rotate against the saw teeth, causing the saw gear to rotate in a clockwise direction, causing the rod and the saw to rotate in the clockwise direction to the third position;

a disc cap joined with the disc and concentrically encircling the drill shaft; and an interconnecting lever defined by an actuation end and a cap end joined with the disc cap, the interconnecting lever pivotally articulating about a hinge, whereby depressing the actuation end of the interconnecting lever displaces the disc towards the motorized drill, causing the saw to rotate in the anticlockwise direction to the second position, whereby lifting the actuation end of the interconnecting lever displaces the disc away from the motorized drill, causing the saw to rotate in the clockwise direction to the third position.

2. The device of claim 1, wherein the longitudinal cutting member comprise a cylindrical shape.

3. The device of claim 1, wherein the longitudinal cutting member comprises a cutting member shoulder.

4. The device of claim 1, wherein the longitudinal cutting member forms a drill tunnel extending through the wall.

5. The device of claim 1, wherein the rod passes through the drill tunnel.

6. The device of claim 1, wherein the lower end of the longitudinal cutting member comprises an open vertical window for accommodating the rod.

7. The device of claim 1, wherein the disc forms a hole sized and dimensioned to receive the drill shaft.

8. The device of claim 1, wherein the saw comprises a tip end and a base end joined with the bottom end of the rod.

9. The device of claim 1, wherein the helical member comprises a calibrated threaded screw.

10. The device of claim 1, wherein the hinge is disposed on the motorized drill.

11. The device of claim 1, wherein the actuation end of the interconnecting lever comprises a handle.

12. The device of claim 1, wherein the interconnecting lever is pivotable relative to a recess of the disc cap.

13. The device of claim 1, further comprising a U-shaped connecting member joined with the cap end of the interconnecting lever.

14. The device of claim 13, wherein the disc cap is defined by a recess that receives the U-shaped connecting member.

15. The device of claim 1, further comprising a gauge scale between the actuation end of the interconnecting lever and the motorized drill.

16. The device of claim 1, further comprising a vertical gauge disposed along the length of the longitudinal cutting member.

17. A device for autogenous bone grafting, the device consisting of:
a cylindrical longitudinal cutting member being defined by an upper end and a lower end forming an opening to a cavity, the longitudinal cutting member further being defined by a wall forming a wall space, the lower end of the longitudinal cutting member comprising a plurality of cutting teeth, the longitudinal cutting member being rotatable about a longitudinal axis;

a drill shaft joined with the upper end of the longitudinal cutting member, the drill shaft being substantially aligned with the longitudinal axis of the longitudinal cutting member;

a motorized drill joined with the drill shaft, the motorized drill rotatably driving the drill shaft and the longitudinal cutting member, whereby the cutting teeth of the longitudinal cutting member are operable to enable longitudinal cutting through a bone;

a rod being defined by a top end and a bottom end, the rod being rotatable about a pivoting axis, the pivoting axis being disposed in a spaced-apart, parallel relationship with the longitudinal axis;

at least one saw joined with the bottom end of the rod, proximal to the lower end of the longitudinal cutting member, the saw being rotatable along a plane perpendicular to the pivoting axis, whereby the saw is operable to enable transversal cutting through the bone whereby the saw rotatably articulates along the plane between a first position substantially inside the wall space of the wall, and a second position extended between the wall and the longitudinal axis of the longitudinal cutting member whereby the saw rotatably articulates along the plane between the first position and a third position partially extended between the wall space and an external area outside the cavity of the longitudinal cutting member;

a saw gear defined by a plurality of saw teeth, the saw gear joined with the top end of the rod;

a disc being in engagement with the drill shaft, the disc being configured to advance along the drill shaft towards the motorized drill, the disc further being configured to advance along the drill shaft away from the motorized drill, the disc comprising disc teeth disposed in meshed engagement with the saw teeth;

a spring disposed around the drill shaft, the spring biasing the disc away from the motorized drill to the first position;

a helical member disposed in the hole of the disc, the helical member being in engagement with the disc and the drill shaft, whereby the helical member causes the disc to rotate clockwise while advancing towards the motorized drill, whereby the helical member causes the disc to rotate counterclockwise while advancing away from the motorized drill, whereby when the disc advances along the drill shaft towards the motorized drill, the disc teeth rotate against the saw teeth, causing the saw gear to rotate in an anticlockwise direction, causing the rod and the saw to rotate in the anticlockwise direction to the second position, whereby when the disc advances along the drill shaft away from the motorized drill, the disc teeth rotate against the saw teeth, causing the saw gear to rotate in a clockwise direction, causing the rod and the saw to rotate in the clockwise direction to the third position;

a disc cap joined with the disc and concentrically encircling the drill shaft, the disc cap forming a recess;

an interconnecting lever defined by an actuation end and a cap end joined with the disc cap, the interconnecting lever pivotally articulating about a hinge, whereby depressing the actuation end of the interconnecting lever displaces the disc towards the motorized drill, causing the saw to rotate in the anticlockwise direction to the second position, whereby lifting the actuation end of the interconnecting lever displaces the disc away from the motorized drill, causing the saw to rotate in the clockwise direction to the third position;

a U-shaped connecting member joined with the cap end of the interconnecting lever, wherein the recess in the disc cap receives the U-shaped connecting member;

a gauge scale between the actuation end of the interconnecting lever and the motorized drill; and a vertical gauge disposed along the length of the longitudinal cutting member.

18. The device of claim 17, wherein the longitudinal cutting member comprises a cutting member shoulder.

19. The device of claim 17, wherein the longitudinal cutting member forms a drill tunnel extending through the wall.

20. A method for autogenous bone grafting, the method comprising:

identifying an entry point proximal to a bone;

cutting an incision through the skin at the entry point;

positioning an autogenous bone grafting device proximal to the entry point, the device comprising a longitudinal cutting member defined by a central longitudinal axis, a lower end having cutting teeth, a wall forming a wall space and a cavity, the device further comprising a saw rotatable about a plane perpendicular to the longitudinal axis, the saw being biased to a first position inside the wall space;

rotatably driving, with a motorized drill, the longitudinal cutting member through the bone, whereby the cutting teeth of the longitudinal cutting member longitudinally cut through the bone;

lifting a pivotally articulating interconnecting lever, the interconnecting lever joined with a disc that is in meshed gear engagement with the saw, whereby longitudinal displacement of the disc causes the saw to rotate about the plane perpendicular to the longitudinal axis;

displacing the disc away from the motorized drill, causing the saw to rotate to a third position partially extended between the wall space and an external area outside the cavity of the longitudinal cutting member, whereby the saw transversally cuts through the bone for external harvesting;

depressing the interconnecting lever;

displacing the disc towards the motorized drill, thereby causing the saw to rotate from the first position in the wall space to a second position towards the longitudinal axis running through the longitudinal cutting member, whereby the saw transversally cuts through the bone for internal harvesting;

lifting the longitudinal cutting member, whereby the saw supports the cut portion of the bone inside the cavity in the longitudinal cutting member; and releasing the interconnecting lever to enable the saw to return to the biased first position inside the wall space, whereby the cut portion of the bone falls through an opening in the lower end of the longitudinal cutting member.

* * * * *